(12) United States Patent
Griffiths et al.

(10) Patent No.: US 9,851,368 B2
(45) Date of Patent: Dec. 26, 2017

(54) KIT AND METHOD FOR QUANTITATIVE DETECTION OF STEROIDS

(71) Applicant: SWANSEA UNIVERSITY, Swansea, West Glamorgan (GB)

(72) Inventors: William Griffiths, West Glamorgan (GB); Yuqin Wang, West Glamorgan (GB); Peter Crick, West Glamorgan (GB); William Bentley, West Glamorgan (GB)

(73) Assignee: SWANSEA UNIVERSITY, Swansea, West Glamorgan (GB)

( * ) Notice: Subject to any disclaimer, the term of this patent is extended or adjusted under 35 U.S.C. 154(b) by 0 days.

(21) Appl. No.: 14/425,548

(22) PCT Filed: Sep. 5, 2013

(86) PCT No.: PCT/GB2013/052324
§ 371 (c)(1),
(2) Date: Mar. 3, 2015

(87) PCT Pub. No.: WO2014/037725
PCT Pub. Date: Mar. 13, 2014

(65) Prior Publication Data
US 2015/0233953 A1   Aug. 20, 2015

(30) Foreign Application Priority Data
Sep. 6, 2012  (GB) .................................... 1215924.0

(51) Int. Cl.
*G01N 33/74* (2006.01)
*G01N 33/92* (2006.01)
*C07C 401/00* (2006.01)

(52) U.S. Cl.
CPC .......... *G01N 33/92* (2013.01); *G01N 33/743* (2013.01); *C07C 401/00* (2013.01); *G01N 2458/15* (2013.01); *G01N 2560/00* (2013.01)

(58) Field of Classification Search
CPC .... G01N 2560/00; G01N 33/92; G01N 33/74; G01N 2458/15; C07C 401/00
See application file for complete search history.

(56) References Cited

U.S. PATENT DOCUMENTS 7,807,472 B2 * 10/2010 Xu ....................... G01N 33/743
435/287.1
2008/0274563 A1 * 11/2008 Cerda .................... G01N 33/64
436/173

(Continued)

FOREIGN PATENT DOCUMENTS

WO        20070140380 A2    12/2007
WO   WO 2007140380 A2 * 12/2007 ........... C07C 269/02

(Continued)

OTHER PUBLICATIONS

William J. Griffiths, Suya Liu, Gunvor Alvelius and Jan Sjövall, "Derivatisation for the characterisation of neutral oxosteroids by electrospray and matrix-assisted laser desorption/ionisation tandem mass spectromety: the Girard P derivative", Rapid Communications in Mass Spectrometry, vol. 17, No. 9, Mar. 19, 2003,924-935.*

(Continued)

*Primary Examiner* — Jennifer Wecker
(74) *Attorney, Agent, or Firm* — Stoel Rives LLP

(57) ABSTRACT

The invention relates to a kit and methods for quantitative detection of steroids in a sample. The kit comprises quantitative charge tags and an oxidizing agent.

16 Claims, 20 Drawing Sheets

(56) References Cited

U.S. PATENT DOCUMENTS

2010/0184095 A1* 7/2010 Haketa ............... G01N 33/6848
435/7.21
2011/0183420 A1 7/2011 Dey et al.
2012/0283137 A1* 11/2012 Baumann .............. C07B 59/002
506/12

FOREIGN PATENT DOCUMENTS

WO 20080137767 A1 11/2008
WO 20100141075 A1 12/2010

OTHER PUBLICATIONS

William J. Griffiths, Suya Liu, Gunvor Alvelius and Jan Sjovall, "Derivatisation for the characterisation of neutral oxosteroids by electrospray and matrix-assisted laser desorption/ionisation tandem mass spectromety: the Girard P derivative", Rapid Communications in Mass Spectrometry, vol. 17, No. 9, Mar. 19, 2003, 924-935.*
International Search Report and Written Opinion for International Application No. PCT/GB2013/052324 dated Sep. 5, 2013, 5 pages.
William J. Griffiths et al: "Discovering Oxysterols in Plasma: A Window on the Metabolome", Journal of Proteome Research, vol. 7, No. 8, Aug. 1, 2008 (Aug. 1, 2008), pp. 3602-3612.
Kersti Karu et al: "Nano-liquid chromatographytandem mass spectrometry analysis of oxysterols in brain: monitoring of cholesterol autoxidation", Chemistry and Physics of Lipids, vol. 164, No. 6, May 6, 2011 (May 6, 2011), pp. 411-424.
Griffiths W J et al: "Analytical strategies for characterization of bile acid and oxysterol metabolomes", Biochemical and Biophysical Research Communications, Academic Press Inc. Orlando, FL, vol. 396, No. 1, May 21, 2010 (May 21, 2010), pp. 80-84.
William J Griffiths et al: "Analysis of oxysterol metabolomes", Biochimica and Biophysica Acta. Molecular and Cell Biology of Lipids, Elsevier, Amsterdam, NL, vol. 1811, No. 11, May 23, 2011 (May 23, 2011), pp. 784-799.
Mirzaei H et al: "Identification and quantification of protein carbonylation using light and heavy isotope labeled Girard's P reagent", Journal of Chromatography. Elsevier Science Publishers B.V. NL. vol. 1134. No. 1-2. Nov. 17, 2006 (Nov. 17, 2006), pp. 122-133.
Toshimasa Toyo' Oka et al: "LC-MS determination of bioactive molecules based upon stable isotope-coded derivatization method", Journal of Pharmaceutical and Biomedical Analysi S. vol. 69.Apr. 25, 2012 (Apr. 25, 2012). pp. 174-184.
William J. Griffiths, Suya Liu, Gunvor Alvelius and Jan Sjövall, "Derivatisation for the characterisation of neutral oxosteroids by electrospray and matrix-assisted laser desorption/ionisation tandem mass spectromety: the Girard P derivative", Rapid Communications in Mass Spectrometry, vol. 17, No. 9, Mar. 19, 2003, 924-935.

* cited by examiner

KIT AND METHOD FOR QUANTITATIVE DETECTION OF STEROIDS

This application is the national stage of international patent application no. PCT/GB2013/052324 filed on Sep. 5, 2013 which in turn claims priority from British Patent Application Ser. No. 1215924.0 filed on Sep. 6, 2012, the disclosures of which are incorporated herein by reference in their entirety.

TECHNICAL FIELD

The present invention relates to a kit for the quantitative detection of steroids and to methods for using the kit. In particular, the method relates to a kit which enables steroids to be quantitatively detected using mass spectrometry.

BACKGROUND

Global steroid analysis of biological samples is challenging. This is on account of the extreme diversity of steroid natural products, the tendency of a single steroid (or small group of steroids) to dominate in abundance over all others, the lack of a strong chromophore or readily ionised functional group, and the general scarcity of quantitative standards.

Steroids are molecules based on the cyclopentanoperhydrophenanthrene skeleton:

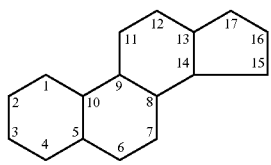 [SMILES: C1CCC2C(C1)CCC1C3CCCC3CCC21]

In vertebrates cholesterol, which has the following structure:

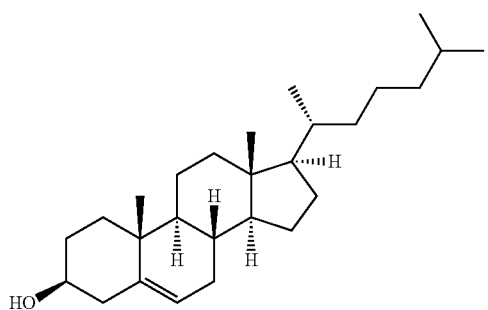

is the dominating steroid. This sterol is metabolised via oxidation to oxysterols and subsequently to biologically active bile acids/alcohols or hormonal steroids (Sjövall et al, 2011 "Analysis of bile acids" in *Steroid Analysis*, H L Makin and D B Gower, Ed., Springer 837-966). Every cell has the capacity to synthesise cholesterol, and many also have the ability to metabolise it through cholesterol hydroxylases and subsequently other enzymes. There are a numerous enzymes involved in cholesterol metabolism, many of which accept multiple substrates with the consequent production of a diverse array of products with known or unknown biological activities (Griffiths, W. J. and J. Sjövall, 2010 *Biochem. Biophys. Res. Commun.*, 396, 80-84). The major steroidogenic organs in mammals are the liver, the brain, the lung, the adrenal cortex and the gonads, and essentially all biosynthetic steroids can be found in the circulation. Sterols such as cholesterol are present in blood as free molecules and esterified to fatty acids, both forms being bound to plasma proteins. Steroids such as dehydroepiandrosterone (DHEA) are esterified with sulphuric acid, while bile acids are usually amidated with glycine or taurine. The conjugation of steroids with small molecules greatly increases the potential complexity of the steroid pool.

The potent biological activity of many steroids has encouraged the development of analytical methods to allow their detection and quantification in biological samples. Mass spectrometry (MS) has proved an effective method for steroid analysis when liked to either gas chromatography (GC) or liquid chromatography (LC). However, both GC-MS and LC-MS have their limitations. For example, GC-MS is intolerant to steroid sulphates or cholesterol esters on account of their lack of volatility, requiring solvolysis or hydrolysis before derivatisation, while LC-MS tends to be insensitive to neutral steroids and fragment-ion spectra are often uninformative. The gold standard method for quantification of steroids is isotope dilution mass spectrometry; this is optimally performed with a stable-isotope labelled standard for each analyte. However, while this is realistic proposition for targeted analysis, it becomes impractical for global approaches.

In earlier studies, we have adopted an LC-MS approach to steroid analysis, but combined the approach with oxidation followed by chemical derivatisation to enhance sensitivity (Karu et al, *J. Lipid Res.* (2007) 48, 976-987). However, although the sensitivity of the method is enhanced, the similarity of steroid structures means that it is still extremely difficult to distinguish steroid molecules from one another. In particular, it is not possible to distinguish a 3β-hydroxy-5-ene sterol and its corresponding 3-oxo-4-ene analogue without repeating the method with no oxidation step.

The present invention overcomes these problems by incorporating the use of quantitative charge tags based on Girard P and Girard T reagents. Quantitative charge tags are known; for example Thompson et al, *Anal. Chem.*, (2003), 75(8), 1895-1904 and Ross et al, *Mol. Cell Proteomics*, (2004), 3(12), 1154-1169 describe the use of tandem mass tags and isobaric mass tags for quantifying proteins. However, the approach has not previously been applied to the quantitative detection of steroids. This is probably because steroids lack an appropriate functional group for specific derivatisation although hydroxyl groups can be derivatised, there is very little biological specificity.

SUMMARY

The present invention combines the two approaches discussed above with novel quantitative charge tags and novel methods for steroid analysis.

In the present invention there is provided a kit for detecting steroids, the kit comprising:

i. at least one pair of quantitative charge tags based on a compound of formula (I) or a compound of formula (II):

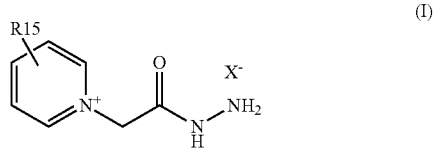

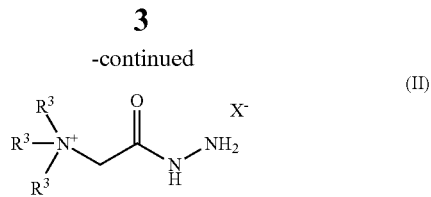

(II)

wherein R is hydrogen, $C_{1-4}$ alkyl or aryl, $OR^1$ or $NR^1R^2$;
each $R^1$ and $R^2$ is $C_{1-3}$ alkyl or $R^1$ and $R^2$ together with the nitrogen atom to
which they are attached form a 5- or 6-membered heteroalkyl ring;
each $R^3$ is independently $C_{1-3}$ alkyl;
X is a halide ion; and
ii. an agent capable of oxidising an OH group at the steroid 3-position to a ketone.

The kit of the present invention has the advantages that it can be used both for the labelling of steroids which contain a ketone group and steroids which do not contain a ketone group but which have an OH group which can be oxidised to give a ketone. Quantitative detection of both types of steroids can be carried out in a single liquid chromatography-mass spectrometry (LC-MS) and/or tandem mass spectrometry (MS/MS) run.

In the present invention the term "$C_{1-4}$ alkyl" refers to a straight or branched chain fully saturated hydrocarbon chain having from 1 to 4 carbon atoms. Examples are methyl, ethyl, n-propyl, isopropyl, n-butyl, sec-butyl or t-butyl. Similarly, the term "$C_{1-3}$ alkyl" refers to an alkyl group having from one to three carbon atoms.

The term "heteroalkyl ring" refers to a saturated or partially unsaturated ring containing at least one heteroatom. Examples include pyrrole, pyrrolidine, morpholine, pyrroline and imidazole.

The term "halide" refers to fluoride, chloride, bromide or iodide.

Examples of R groups in the compounds of formula (I) include hydrogen, methyl, phenyl, methoxy, ethoxy, dimethyl ammonium, diethyl ammonium, N-pyrrolidinyl and N-piperidinyl.

More suitably, R is hydrogen, methyl, phenyl, methoxy, dimethylamino, N-pyrrolidinyl and N-piperidinyl, especially hydrogen, methoxy, dimethylamino and N-pyrrolidinyl but particularly hydrogen.

In one embodiment of suitable compounds of formula (II), all of $R^3$ groups are the same. In an alternative embodiment two of the $R^3$ groups are the same as one another. In a further alternative embodiment, all of the $R^3$ groups are different. Suitably, $R^3$ is methyl or ethyl, but especially methyl.

In compounds of formulae (I) and (II), X is more suitably chloride or bromide.

In the present invention, the quantitative charge-tags are based on compounds of formula (I) or formula (II). The compound of formula (I) in which R is H is Girard P (GP) reagent (Girard and Sandulesco, 1936). The compound of formula (II) in which each of the $R^3$ groups is methyl is Girard T reagent. The compounds of formulae (I) and (II) have a carbonyl-reactive hydrazine terminal linked through a carboxymethyl group to a charged pyridine ring (formula I) or a trimethylammonium group (formula II).

The quantitative charge-tags react with a ketone group, e.g. at the 3-position of a steroid to give a derivatised molecule. The use of Girard P reagent to derivatise oxysterols and thereby assist the identification of the oxysterols by mass spectrometry is described by Karu et al, *j. Lipid Res*, 48, 976-987 (2007). However, the approach used by the present inventors differs from that used by Karu et al in that it uses pairs of quantitative charge tags to detect different types of sterols in sample and reference compositions.

Table 1 shows a series of quantitative charge tags based on Girard P reagent (i.e. a compound of formula (I) in which R is hydrogen. By reacting [$^2H_5$]pyridine with ethyl bromoacetate and then hydrazine, [$^2H_5$]Girard P ([$^2H_5$]-GP) (ii) is easily synthesized (yield 97%, see examples). Similarly, by utilizing pyridine or [$^{15}N$]pyridine and ethyl [1,2- or 1-$^{13}C$] bromoacetate the isotopomers [$^{13}C_2$]-GP (iii) and [$^{13}C^{15}N$]-GP (iv) are generated. Analogues of (iii) and (iv) can also be synthesized based on the [$^2H_5$]pyridine and [$^2H_5$$^{15}N$]pyridine substrates i.e. [$^2H_5$$^{13}C_2$]-GP (v) and [$^2H_5$$^{13}C^{15}N$]-GP (vi).

TABLE 1

Quantitative Charge Tags based on Girard P Reagent

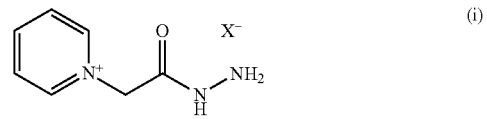

(i)

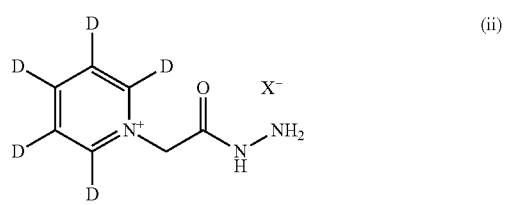

(ii)

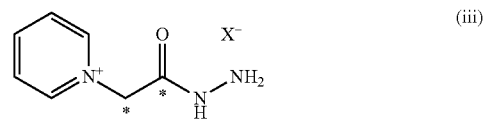

(iii)

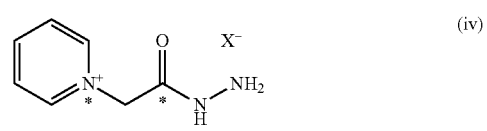

(iv)

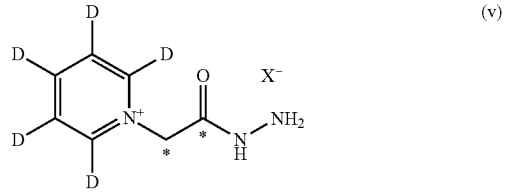

(v)

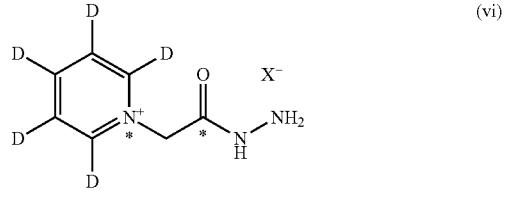

(vi)

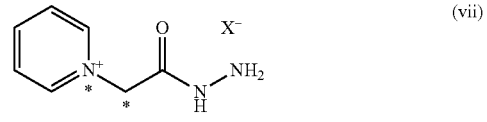

(vii)

TABLE 1-continued

Quantitative Charge Tags based on Girard P Reagent

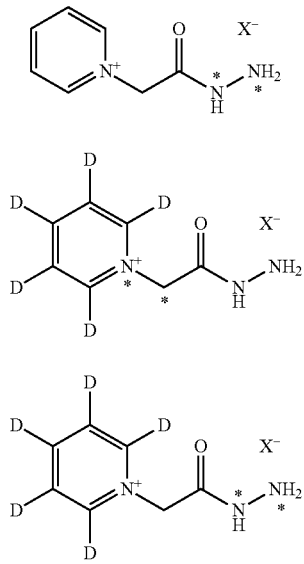

(viii)

(ix)

(x)

where * adjacent to a C atom represents $^{13}$C and * adjacent to a N atom indicates $^{15}$N.

Each of the compounds of formula (I) will have a similar group of charge tags to that shown above. It is also possible to design a group of charge tags based on formula (II). This is shown in Table II.

TABLE 2

Quantitative Charge Tags based on Girard T Reagent

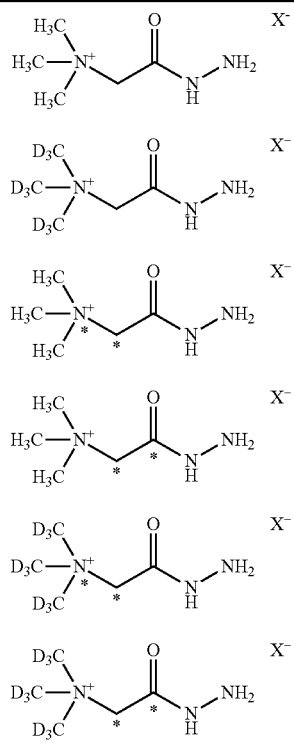

TABLE 2-continued

Quantitative Charge Tags based on Girard T Reagent

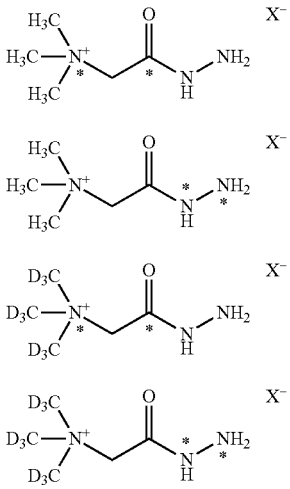

where * adjacent to a C atom represents $^{13}$C and * adjacent to a N atom indicates $^{15}$N.

Full details of the synthesis of the quantitative charge-tags are provided in the examples. The compound of formula (II) and its $^2$H, $^{15}$N and $^{13}$C variants can be synthesised in a similar manner.

The quantitative charge tags used in the kit of the present invention fall into two groups. The first group is differential mass tags in which one or more hydrogen atoms in a compound of formula (I) or (II) is replaced by deuterium or tritium, more usually by deuterium. Generally, in the compounds of formula (I), the pyridine hydrogen atoms will be replaced by deuterium and in the compounds of formula (II), the hydrogen atoms of the trimethylammonium group will be replaced by deuterium. The pair of differential mass tag molecules are identical in all other respects. Examples of pairs of differential mass tags in the compounds of Table 1 are: (i) against (ii), or (iii) against (v), or (iv) against (vi).

Differential mass tags can be used as derivatisation agents to quantitate one sample against another by exploiting their differing mass (Δ5 Da) but otherwise essentially identical physical and chemical properties, i.e. LC retention time, and MS sensitivity.

The differential mass tags exploit deuterium labelling in the pyridine ring of the GP reagent of formula (I), where the mass difference between the heavy (e.g. ii of Table 1) and light (e.g. i of Table 1) tags is 5 Da for Compounds of formula (I) where R is hydrogen; or 4 Da for compounds of formula (I) where R is not hydrogen. In compounds of formula (II), the mass difference between heavy and light tags will be 9 Da (see Table 2).

The essentially identical chemical properties of the heavy and light tags means that they react with substrates at an identical rate, giving essentially identical products but differing in mass. This mass difference allows the differentiation of substrates by MS. The mass difference can be exploited in a number of ways. Firstly, to simplify the steroid charge-tagging methodology that otherwise requires duplicate LC-MS analysis of enzyme-treated and enzyme-free samples. By utilising heavy tags (ii of Table 1) to derivatise enzyme-treated and light tags (i of Table 1) to derivatise enzyme-free samples, or vice versa, and then combining the samples prior to LC-MS analysis, only a single analysis is required (FIGS. 1C & 3). This avoids problems caused by chromatographic deterioration between injections, differing ESI efficiency between runs, and particularly important for plasma analysis, matrix effects caused by periodic discharge of bound phospholipids from the column. Throughput is also doubled and instrument time halved. Using quantitative charge-tags in a differential mass tag format over 40 steroids can be quantitatively detected in a single run (see Table S1). A second application of differential mass tags is to discriminate between samples prepared in an identical fashion but derived from different patient groups.

There are two main disadvantages of the differential mass tag protocol. Firstly, it is preferentially performed on mass spectrometers at high resolution, necessary to resolve peaks of interest from others of similar mass in the complex mixture. This is particularly important for low abundance analytes, e.g. dihydroxycholesterols. The second disadvantage is that the complexity of the mass spectrum is increased, and analyte signal divided over two peaks. Again, this is important for low abundance compounds as the concentration of injected sample is necessarily reduced by half compared to the situation where only a single tagged sample is injected. In order to mitigate these disadvantages, the present inventors have also developed a second type of quantitative charge-tag.

The second type of quantitative charge tags are isobaric mass tags. In this group both of the isobaric mass tags have the same molecular mass but one of the pair of isobaric mass tags contains a $^{15}N$ moiety while the other contains a $^{13}C$ moiety, with the remainder of the molecules being identical. Both members of the isobaric mass tag pair may contain additional $^{13}C$ atoms or may contain deuterium atoms. Examples of pairs of isobaric mass tags in Table 1 are (iii) against (iv), and (v) against (vi).

Incorporation of isobaric mass tags by derivatisation adds essentially the same mass to the substrate molecules. In this case tagged samples can be differentiated from one another following MS fragmentation i.e. tandem mass spectrometry (MS/MS of $MS^n$). For example molecules tagged with $[^{13}C_2]$-GP (iii of Table 1) can be differentiated from and quantitated against those tagged with $[^{13}C^{15}N]$-GP (iv of Table 1) based on the abundance of the $[M-Py]^+$ ions where Py will be 79 Da in $[^{13}C_2]$-GP (iii of Table 1) and 80 Da in $[^{13}C^{15}N]$-GP (iv of Table 1).

In isobaric mass tags, differences in the isotope-labelled tags are evident at the MS/MS or $MS^n$ level, and the tags can be exploited for similar applications to the differential mass tags. With isobaric mass tags of formulae (I) and (II) a mass difference of 1 Da is evident at the MS/MS or $MS^2$ level in the mass of $[M-Py]^+$ fragment-ions (formula I) or $[M-NR^3_3]^+$, e.g. $[M-NMe_3]^+$ fragment ions (formula II). These fragment-ions can then be used for relative quantification between differentially tagged samples (FIG. 4D). The mass-separated $[M-Py]^+$ or $[M-N NR^3_3]^+$ fragment-ions can be fragmented further and quantification additionally be performed at the $MS^3$ level from the respective TICs (FIG. 4E). This also adds structural information to the analysis. Isobaric tags can only be utilised on instruments with MS/MS or $MS^n$ capability, in which case the high resolution mass scan becomes redundant, and quantification is performed at the fragment ion level. While isobaric tags do not complicate the MS scan, and in fact analytes of similar mass from differentially tagged samples reinforce peak intensity, quantification at the MS/MS or $MS^2$ level at low resolution can be distorted by co-eluting analytes undergoing a similar transition. Again this is most important for analytes of low abundance and may distort the measured signal. This can be easily overcome, however, by exploiting high resolution for $MS^2$ peak measurement, or extending the fragmentation scheme one step further to $MS^3$ Advantageously, therefore, the kit of the invention comprises more than one pair of quantitative charge tags; for example the kit may comprise two pairs of quantitative charge tags, for instance a pair of differential mass tags and a pair of isobaric mass tags. In some embodiments, the kit may comprise three, four or five pairs of quantitative charge tags. These will generally be a mixture of differential mass tags and isobaric mass tags.

Advantageously, when the kit comprises more than one pair of quantitative charge tags, all of the quantitative charge tags in the kit will be based upon the same compound of formula (I) or formula (II). This is to ensure that all of the quantitative charge tags in the kit are chemically identical in order that the kit will give consistent and meaningful results.

Although some steroids possess a carbonyl group readily available for derivatisation via coupling to a hydrazine group e.g. hydroxyandrostenone and hydroxyandrostanone isomers, most oxysterols do not. However, many steroids have an OH group at the steroid 3-position which can be oxidised to give a ketone. The kit of the present invention comprises an agent capable of effecting this oxidation reaction, most suitably an agent or mixture of agents capable of oxidising both 3α- and 3β-hydroxy groups. In some embodiments it is preferred that the oxidising agent is selective for the steroid 3-position.

Suitable oxidising agents include enzymatic agents such as a cholesterol oxidase or a cholesterol dehydrogenase enzyme. Suitable cholesterol oxidase enzymes capable of effecting the conversion of 3β-hydroxy groups to 3-ketones can be obtained from *streptomyces* species (MacLachlan et al., 2000). Similarly, 3α-hydroxysteroid dehydrogenase can be used to effect the conversion of 3α-hydroxy substrates to 3-ketones. Typically, therefore, the kit of the present invention will contain one or both of these enzymes.

The kit of the invention can be used to determine the abundance in a steroid-containing sample of steroids which contain a carbonyl group and steroids which contain an OH group capable of oxidation to a carbonyl group. In this method, two identical aliquots of sample (e.g. plasma) are worked-up in parallel, either with or without enzymatic oxidation, and then derivatised with two different quantitative charge tags, e.g. $[^2H_0]$-GP (i of Table 1) and $[^2H_5]$-GP (ii of Table 1), respectively, or vice versa. The derivatised aliquots are then combined and analysed by LC-MS. The intensity of peaks generated from the non-oxidised aliquot provides a measure of the abundance of steroids naturally possessing a carbonyl group, while the intensity of co-eluting peaks from the oxidised aliquot provides the combined abundance of steroids oxidized to contain a carbonyl group and those naturally possessing one. The abundance of steroids oxidized to contain a carbonyl group can then be determined by the difference.

Thus, in a second aspect of the invention, there is provided a method for the quantitative detection in a sample containing steroids comprising a carbonyl group and steroids comprising a hydroxyl group capable of oxidation to a carbonyl group, the method comprising:

i. reacting a first portion of the sample with a first member of a pair of quantitative charge tags of formula (I) or formula (II) as defined above;

ii. reacting a second portion of the sample with an agent capable of oxidising an OH group to a carbonyl group;

iii. reacting the product of step (ii) with a second member of a pair of quantitative charge tags of formula (I) or formula (II) as defined above;

iv. combining the products of steps (i) and (iii);

v. conducting mass spectrometry on the combined product of step (iv) and determining the quantities therein of compounds labelled with the first and second members of the pair of quantitative charge tags.

In this method:

the total amount of steroid labelled with the first member of the pair of quantitative charge tags represents the amount of steroid in the first portion possessing a carbonyl group; and the total amount of steroid labelled with the second member of the pair of quantitative charge tags represents the amount of steroid in the second portion which contains either a ketone group or an OH group at the steroid 3-position.

If the volumes of the first and second portions of the sample are known, the total quantity of steroids containing a ketone group and steroids containing a 3-OH group can be calculated. For simplicity, it is generally preferred that the first and second portions of the sample are of equal volume.

The pair of quantitative charge tags may be either differential mass tags or isobaric mass tags. When differential mass tags are used, the mass spectrometry of step (v) will comprise liquid chromatography-mass spectrometry (LC-MS) or HPLC-MS. When isobaric mass tags are used, the mass spectrometry of step (v) will be an LC-MS/MS method.

The sample may be any solution of steroids but will often be a sample obtained from a natural source, e.g. a plant or animal source, which it is necessary to analyse. The kit and methods of the present invention are particularly useful for analysing samples derived from animals, for example mammals and especially humans. In this case, the sample may be a body fluid, for example whole blood, plasma, serum, cerebrospinal fluid, sputum, tears, sweat or urine. However, in many cases, it is preferable to prepare a sample from a body fluid by extraction of the steroids before reaction with a quantitative charge tag or with an oxidising agent and a quantitative charge tag. Alternatively, a sample may be prepared by extracting steroids from a specimen of tissue, hair, nails etc.

Suitably, a sample may be prepared by extracting the steroids from a body fluid such as plasma into a suitable solvent, for example ethanol. This may be done by adding the body fluid to ethanol, typically absolute ethanol.

Cholesterol represents the dominating steroid in plasma and is more than a million times more abundant than most oxysterols. As a consequence of its autoxidation during sample handling or storage cholesterol can generate numerous artefact oxysterols as well as $C_{19}$ and $C_{21}$ steroids (Liere et al, 2009 *J. Lipid Res.* 50, 2430-2444; Schroepfer, Jr., 2000 *Physiol Rev.* 80, 361-554). To avoid this potential problem, the preparation of the sample for use in the methods of the present invention suitably includes the step of separating cholesterol from more polar steroids on a reversed-phase (RP) solid phase extraction (SPE) column immediately after steroid extraction into ethanol. Nonpolar sterols e.g. cholesterol, are then analysed separately from oxysterols and side-chain shortened steroids.

The kit of the present invention may be used in combination with a reference composition. The kit may therefore comprise a reference composition. Alternatively, however, a reference composition may be supplied separately or may be prepared by a user.

The nature of the reference composition depends upon the purpose for which the kit is intended.

Thus, if the kit is intended to detect particular steroids, for example when used as a drug testing kit for athletes or as a diagnostic test for a particular disease, the reference composition may comprise one or more known steroids in known quantities so that the sample can be compared with the reference composition and quantitative detection of target steroids can be carried out.

However, for global steroid analysis, it is not practical to obtain pure authentic samples of all steroids potentially present in a sample, for example a plasma sample. Therefore, rather than obtain a library of pure compounds and combine them in known amounts to make a calibration mix for the global quantitative steroid analysis of a sample, an alternative strategy, particularly useful for comparative analysis of samples, is to generate a master mix, or quality control sample.

In this case, the reference composition comprises a master mix made up of pooled reference samples of the same type as the sample. For example, when the intended sample is plasma, the master mix comprises pooled plasma samples from a number of sources. Similarly, when the intended sample is urine, the master mix may comprise pooled urine samples, etc.

Therefore, in a further aspect of the invention there is provided a method for the quantitative detection of steroids in a sample, the method comprising:

i. reacting the sample with a first member of a pair of quantitative charge tags of formula (I) or formula (II) as defined above;

ii. reacting a reference composition with a second member of a pair of quantitative charge tags of formula (I) or formula (II) as defined above;

iii. combining the products of steps (i) and (ii);

iv. conducting mass spectrometry on the combined product of step (iii) and determining the quantities therein of compounds labelled with the first and second members of the pair of quantitative charge tags.

This method provides data on steroids naturally possessing a ketone group.

Optionally, both the sample and the reference composition may be reacted with an agent capable of oxidising an OH group to a carbonyl group before reaction with the quantitative charge tags; this provides data on steroids which do not naturally possess a ketone group. Quantitative data on compounds with a free OH group at C-3 can then be obtained by difference in the values obtained from the method with and without oxidation.

Thus, the method which includes the oxidation of sample and reference composition comprises the steps of:

i. reacting the sample with an agent capable of oxidising an OH group to a carbonyl group;

ii. reacting the product of step (i) with a first member of a pair of quantitative charge tags of formula (I) or formula (II) as defined above;

iii. reacting a reference composition with an agent capable of oxidising an OH group to a carbonyl group;

iv. reacting the product of step (iii) with a second member of a pair of quantitative charge tags of formula (I) or formula (II) as defined above;

v. combining the products of steps (ii) and (iv);

vi. conducting mass spectrometry on the combined product of step (v) and determining the quantities therein of compounds labelled with the first and second members of the pair of quantitative charge tags.

This method therefore provides an illustration of the differences in the steroid content of the sample and the reference composition. It is possible to determine whether the sample contains the same or different steroids from the reference composition and also to determine whether the steroid compounds are present in different quantities in the sample and reference composition. Therefore, in order to simplify the method as much as possible, it is preferred that the sample and the reference composition are of equal volume.

As with the method described above, the pair of quantitative charge tags may be either differential mass tags or isobaric mass tags. When differential mass tags are used, the mass spectrometry of step (v) will comprise liquid chromatography-mass spectrometry (LC-MS) or HPLC-MS. When isobaric mass tags are used, the mass spectrometry of step (v) will be an MS/MS method.

In some embodiments, this method may be used to determine differences in the steroid content of samples from patients with different conditions. For example, the sample in the method above may comprise individual or pooled samples from patients with a medical condition which is under investigation, for example a condition such as Alzheimer's disease or mild cognitive impairment. In this case, the reference composition may comprise pooled samples from patients not suffering from the condition or from patients suffering from a similar condition so that samples can be compared. Thus, when the sample comprises individual or pooled samples from patients with Alzheimer's disease, the reference sample may comprise pooled samples from patients suffering from the disease, mild cognitive impairment or it may be a control sample comprising pooled samples from patients not suffering from either condition.

Thus, if an investigator wishes to compare first and second medical conditions, the method set out above may be carried out in three iterations as follows:

in a first iteration, the sample may comprise individual or pooled samples from patients suffering from the first condition and the reference composition may comprise pooled samples from patients not suffering from either the first or the second condition;

in a second iteration, the sample may comprise individual or pooled samples from patients suffering from the second condition and the reference composition may comprise pooled samples from patients not suffering from either the first or the second condition; and in a third iteration, the sample may comprise individual or pooled samples from patients suffering from the first condition and the reference composition may comprise pooled samples from patients suffering from the second condition.

The inventors have used this approach to compare pooled control plasma with plasma pools from Alzheimer's disease (AD) and mild cognitive impairment (MCI) patients. In this method, control plasma was oxidized and derivatised with [$^2$H$_0$]-GP reagent (i of Table 1), while AD plasma was oxidized and derivatised with [$^2$H$_5$]-GP (ii), or vice versa. The samples were combined and analysed by LC-MS. MCI plasma is then be oxidized and derivatised with [$^2$H$_5$]-GP (ii of Table 1) and analysed against control. The triangle is then completed by oxidizing and derivatising a second aliquot of MCI plasma with [$^2$H$_0$]-GP reagent (i of Table 1) and combining it with [$^2$H$_5$]-GP (ii of Table 1) labelled AD plasma.

In another embodiment, the method may be used to determine differences in the steroid content of a sample when compared with a reference composition.

The method of this embodiment may be used, for example to investigate medical conditions known to be associated with changes in steroid concentrations in the blood. Examples of such conditions include defects in cholesterol metabolism but also other conditions associated with steroid abnormalities such as Alzheimer's disease and mild cognitive impairment, Parkinson's disease, motor neuron disease, and bacterial and viral infections The method of this embodiment may also be used in sport to detect steroids in samples of blood, urine, tears, sputum, sweat and hair. In this case, the reference composition may comprise pooled samples from a general population or a population known not to have been exposed to steroids.

The inventors have used a master mix as a reference composition for the rapid screening of individual samples from patients with suspected defects in cholesterol metabolism. By labelling the master mix with [$^2$H$_0$]-GP reagent (i of Table 1) and patient sample with [$^2$H$_5$]-GP (ii of Table 1), or vice versa, and then combining the samples for LC-MS analysis differences in the abundance of any of over forty different metabolites can be detected. This is illustrated here with patients suffering from oxysterol 7α-hydroxylase deficiency, cerebrotendinous xanthomatosis (CTX) and Smith-Lemli-Optiz syndrome (SLOS) characterized by mutations in the CYP7B1 (Setchell et al, 1998, *J. Clin. Invest* 102, 1690-1703), CYP27A1 (Björkhem and Hansson, 2010, *Biochem. Biophys. Res. Commun.* 396, 46-49) and DHCR7 (Tint et al, 1994, *N. Engl. J. Med.* 330, 107-113.) genes, respectively. An alternative labelling strategy is to utilise isobaric tags and label the master mix with e.g. [$^{13}$C$_2$]-GP (iii of Table 1) and the patient sample with [$^{13}$C$^{15}$N]-GP (iv of Table 1), or vice versa, and perform relative quantification at the MS/MS or MSn level.

In a further method of the present invention the reference composition may be used in a multiplex combination with quantitative charge-tags.

Therefore, the invention provides a method for the quantitative determination of steroids in a sample comprising:

i. reacting a first portion of the sample with a first member of a first pair of quantitative charge tags of formula (I) or formula (II) as defined above;

ia. reacting a first portion of a reference composition with a first member of a second pair of quantitative charge tags of formula (I) or formula (II) as defined above;

ii. reacting a second portion of the sample with an agent capable of oxidising an OH group to a carbonyl group;

iia reacting a second portion of a reference composition with an agent capable of oxidising an OH group to a carbonyl group;

iii. reacting the product of step (ii) with a second member of a first pair of quantitative charge tags of formula (I) or formula (II) as defined above;

iiia reacting the product of step (iia) with a second member of a second pair of quantitative charge tags of formula (I) or formula (II) as defined above iv. combining the products of steps (i) and (iii);

v. conducting mass spectrometry on the combined product of step (iv) and determining the quantities therein of compounds labelled with the first and second members of the pairs of quantitative charge tags.

This corresponds to a method of the second aspect of the invention comprising the additional steps of:

ia. reacting a first portion of a reference composition with a first member of a second pair of quantitative charge tags of formula (I) or formula (II) as defined above;

iia reacting a second portion of a reference composition with an agent capable of oxidising an OH group to a carbonyl group;

iiia reacting the product of step (iia) with a second member of a second pair of quantitative charge tags of formula (I) or formula (II) as defined above; and combining the products of steps (ia) and (iiia) with the mixture of step (iv) above before carrying out step (v) above, (i.e. conducting mass spectrometry on the combined product and determining the quantities therein of compounds labelled with the first and second members of the first pair of quantitative charge tags and the first and second members of the second pair of quantitative charge tags).

Usually, one of the pairs of quantitative charge tags is a pair of differential mass tags, while the other is a pair of isobaric mass tags. In this case, the sample is analysed both by LC-MS or HPLC-MS and also by MS/MS.

In an example of this method, aliquots of control plasma are labelled by e.g. [$^2H_5$$^{13}C_2$]-GP (v of Table 1) and [$^2H_5$$^{13}C^{15}N$]-GP (vi of Table 1) with and without cholesterol oxidase treatment, respectively. Patient plasma can be similarly derivatised with and without cholesterol oxidase treatment and labelled with [$^{13}C_2$]-GP (iii of Table 1) and [$^{13}C^{15}N$]-GP (iv of Table 1), respectively. Equal aliquots of the four derivatised samples are then combined and analysed by LC-MS with MS/MS or MS$^n$. The mass spectra will give a measure of the relative abundance of metabolites between control and patient samples, while the MS/MS or MS$^n$ spectra will deconvolute the metabolites into those naturally possessing a carbonyl group and those derivatised to contain one.

Multiplexing can be further extended by including further samples or reference compositions labelled with additional quantitative charge tags based on compounds of formula (I) or formula (II), for example [$^2H_0$]-GP (i of Table 1) and [$^2H_5$]-GP (ii of Table 1).

Suitably the volumes of all the portions of sample and reference solution are equal for ease of comparison of steroid types and concentrations.

Furthermore, the charge tags used in the multiplex method described above are usually all based on the same compound of formula (I) or formula (II) since all the charge tags will then be chemically identical. Thus, the quantitative charge tags used are generally all part of a group, for example the groups shown in Tables 1 and 2 above.

BRIEF DESCRIPTION OF THE DRAWINGS

The invention will now be described in greater detail with reference to the examples and to the drawings in which.

DETAILED DESCRIPTION

EXAMPLES

Material

Authentic sterols were purchased from Avanti Polar Lipids (Alabaster, Ala.) or Sigma Aldrich and stored at −20° C. until use. HPLC water and HPLC grade solvents were purchased from Fisher Scientific. GP reagent (chloride salt) was purchased from TCI Europe (Oxford, UK). Cholesterol oxidase from *Streptomyces* sp. was from Sigma Aldrich. Certified Sep-Pak C$_{18}$ cartridges were from Waters (Elstree UK). All other chemicals and reagents were purchased from Sigma Aldrich or Fisher Scientific and used as received unless otherwise stated. Blood plasma samples were from St Mary's Hospital, Manchester, Institute of Child Health, London or from a GlaxoSmithKline study and were provided with institutional review board and ethical approval.

Example 1—Synthesis of Quantitative Charge-Tags

The isotope-labelled quantitative charge-tags were synthesized from pyridine, ethyl bromoacetate and hydrazine as illustrated in Scheme 1 with high yields (97%).

Scheme 1

To a solution of pyridine (1.0 mL, 11.6 mmol) in ethanol (10 mL), ethyl bromoacetate (1.51 mL, 11.6 mmol) was added dropwise. The resulting mixture was heated at reflux for 4 hr then allowed to cool to room temperature then to 0° C. Hydrazine hydrate (80% aqueous solution, 0.73 mL, 11.6 mmol) was added carefully causing a white precipitate to form. The precipitate was recovered by vacuum filtration and dried under reduced pressure to afford the GP reagent (i of Table 1) as a white solid (2.66 g, 11.2 mmol, 97%). Isotope labelled versions of the GP reagent are synthesised in an identical manner but using [$^2$H$_5$]pyridine, ethyl [1,2-$^{13}$C$_2$]bromoacetate, [$^{15}$N]pyridine, ethyl [1-$^{13}$C]bromoacetate, and [$^2$H$_5$$^{15}$N]pyridine (see Table 1).

Figure 1A:
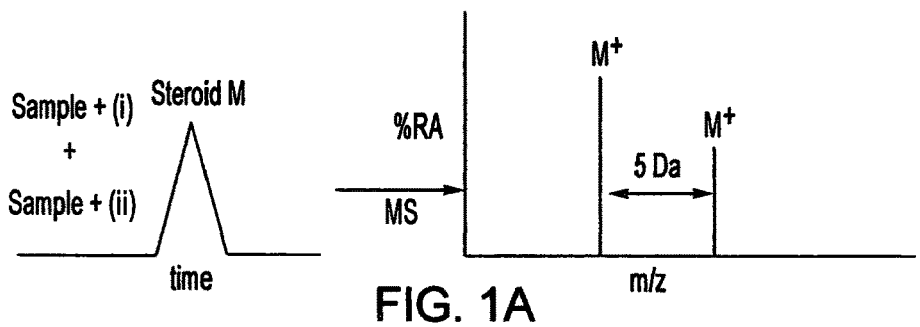
FIG. 1A is a schematic illustration of the design and application of quantitative charge-tags using differential mass tags.
Figure 1B:
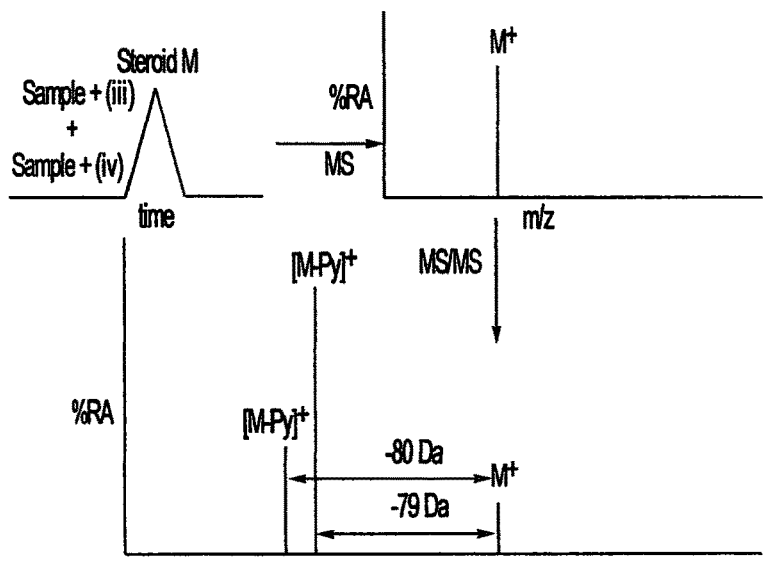
FIG. 1B is a schematic illustration of the design and application of quantitative charge-tags using isobaric mass tags, wherein [M-Py]$^+$ corresponds to the loss of pyridine from the molecular ion [M]$^+$.
Figure 1C:
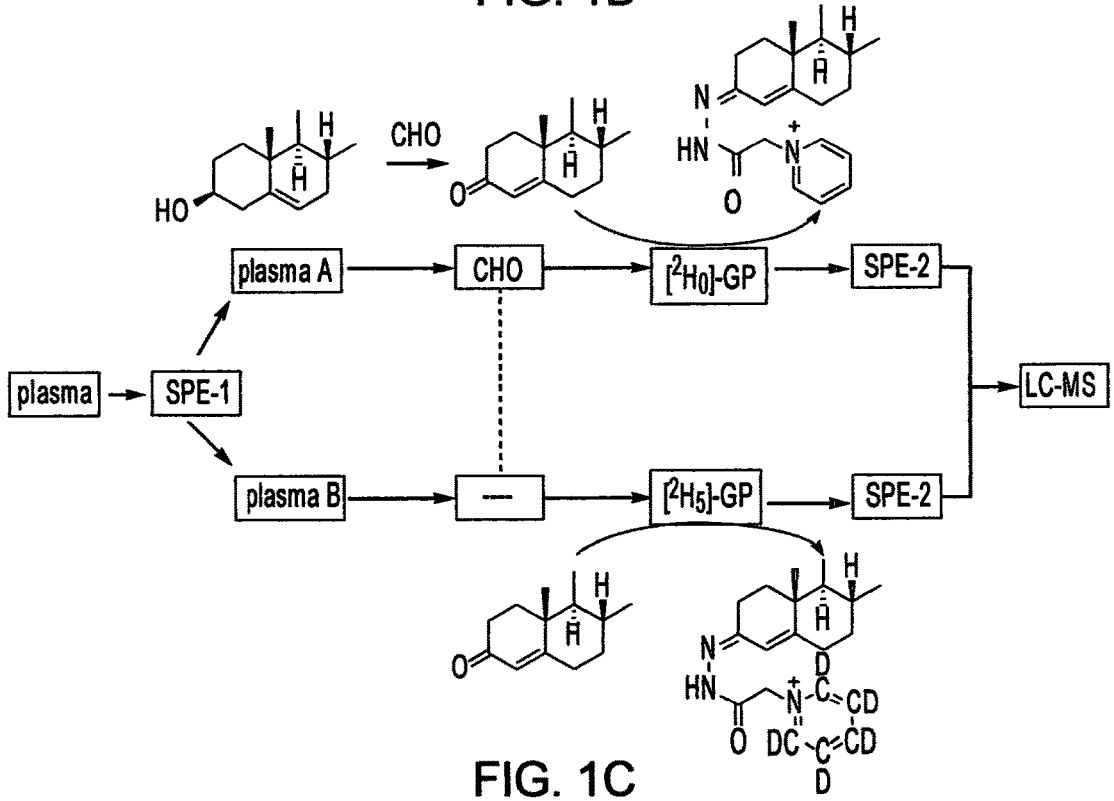
FIG. 1C shows use of quantitative charge-tags to deconvolute steroids oxidised to contain a 3-oxo group from those naturally possessing an oxo group, wherein CHO represents enzymatic oxidation with cholesterol oxidase.
Figure 1E:
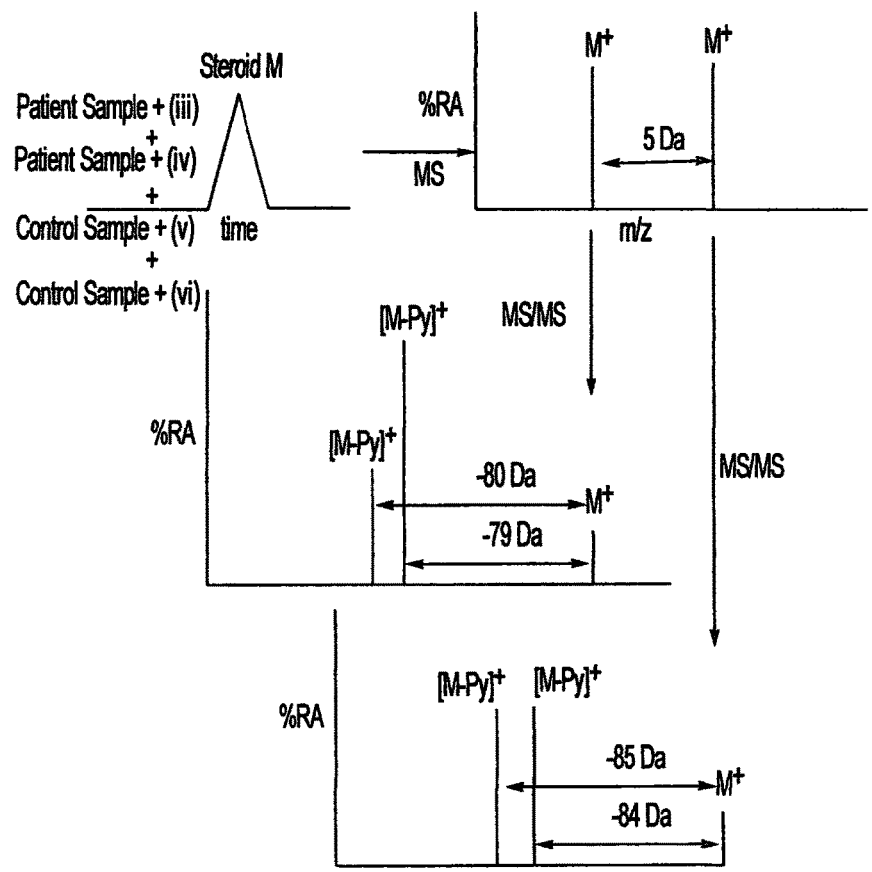
FIG. 1E shows quadruplex use of quantitative charge-tags, wherein plasma samples (e.g. patient and control) are analysed with and without enzymatic oxidation.
Figure 1D:
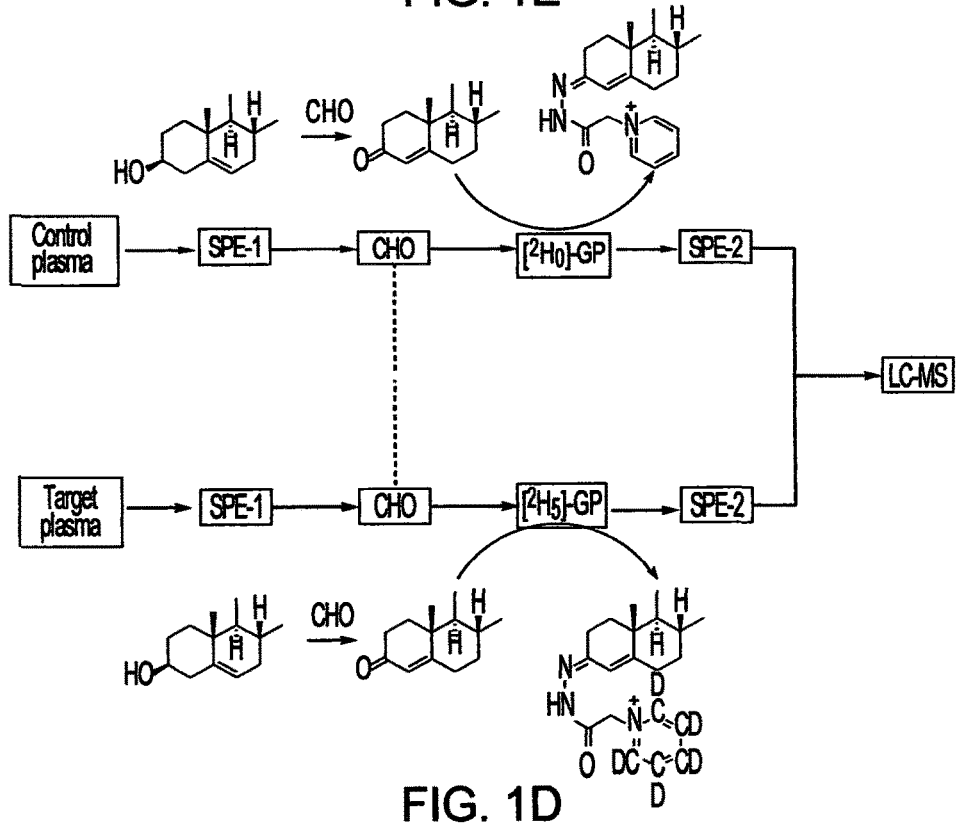
FIG. 1D shows relative quantification of steroids in target (e.g. AD) plasma against control.

Initial synthetic procedures were performed with [$^2$H$_5$] pyridine of 99.5% isotopic purity, this led to 0.5% of the ultimate product (ii of Table 1) being unlabelled. When patient samples were labelled with the GP reagent (ii of Table 1), the presence of unlabelled GP reagent in the reaction mix distorted the signal for metabolites labelled with GP reagent (i of Table 1) from e.g. control samples, when analysed in the same LC-MS run (FIG. 1D). In most cases this distortion was insignificant; however, an exception occurred in the case of patient metabolites being far more abundant than those in control samples. The simplest solution to this problem is to derivatise the patient sample with the non-isotope labelled [$^2H_0$]-GP reagent (i of Table 1) and the control sample with [$^2H_5$]-GP (ii of Table 1). However, we have now altered the synthetic method to use [$^2H_5$]pyridine of 99.96% isotopic purity, essentially eliminating the problem. In fact, the high isotopic impurity of the resultant product with respect to deuterium, in addition to the stability of deuterium on the aromatic ring with respect to H/D exchange are a major advantage of this charge-tag. A similar issue arises with ethyl [1-$^{13}$C and 1,2-$^{13}C_2$] bromoacetate (both 99% $^{13}$C) [$^{15}$N]pyridine (98% $^{15}$N) and [$^2H_5$$^{15}$N]pyridine used to generate the isobaric mass tags iii, iv, v and vi of Table 1. However, by selecting ions corresponding to fully isotope labelled derivatives for MS/MS or MS" the low mass isotopomers are excluded from quantitative measurements minimising the problem (FIG. 1).

Charge-tags based on other compounds of formula (I) may be synthesised using a similar method but using an appropriately substituted pyridine as a starting material.

Charge-tags based on Girard T reagent (formula II) may be synthesised in a similar manner but using trimethylamine instead of pyridine.

Example 2—Extraction of Steroids from Plasma and Blood Spots

Figure 8:
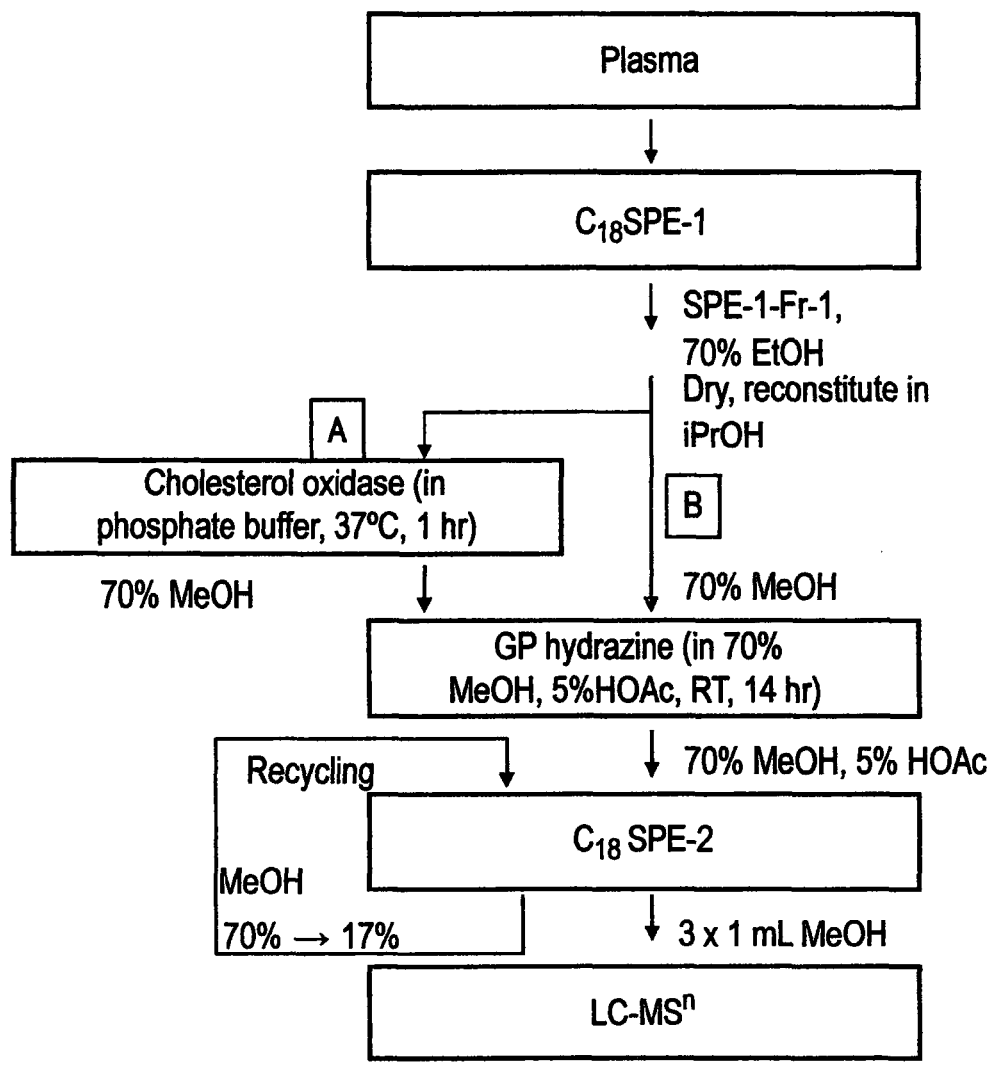
FIG. 8 shows a scheme for the extraction of steroids from plasma.

Plasma (100 µL) was added dropwise to a solution of absolute ethanol (1.05 mL) containing 24(R/S)-[25,26,26,26,27,27,27-$^2H_7$]hydroxycholesterol (or 24(R/S)-[26,26,26,27,27,27-$^2H_6$]hydroxycholesterol) and 22(R)-[25,26,26,26,27,27,27-$^2H_6$]hydroxycholest-4-en-3-one (20 ng of each in 1.05 mL of absolute ethanol) in an ultrasonic bath. After 5 min the solution was diluted to 70% ethanol by addition of 0.35 mL of water, ultrasonicated for a further 5 min and centrifuged at 14 000×g at 4° C. for 30 min. The supernatant was loaded onto a 200 mg Certified Sep-Pak $C_{18}$ cartridge (pre-conditioned with 4 mL of absolute ethanol followed by 6 mL 70% ethanol) and allowed to flow at ~0.25 mL/min. The flow-through was combined with a column wash of 70% ethanol (5.5 mL) to give SPE1-Fr1 containing the oxysterols. A second fraction (SPE1-Fr2) was collected by eluting with a further 4 mL of 70% ethanol before elution of cholesterol and similarly hydrophobic sterols using 2 mL of absolute ethanol (SPE1-Fr3). Each fraction was concentrated under reduced pressure using a vacuum concentrator (ScanLaf, Denmark) (FIG. 8).

Sterols were extracted from blood spots as described in Griffiths et al (Griffiths W J, Wang Y, Karu K, Samuel E, McDonnell S, Hornshaw M, Shackleton C. *Clin Chem.* 2008 August; 54(8):1317-24)

Example 3—Charge Tagging of Steroids from Plasma or Blood Spots

The steroid-containing fractions from Example 2 were re-constituted in 100 µL propan-2-ol then treated with $KH_2PO_4$ buffer (1 mL 50 mM, pH 7) containing 3 µL of cholesterol oxidase (2 mg/mL in $H_2O$, 44 units/mg protein). The reaction mixture was incubated at 37° C. for 1 hr then quenched with 2.0 mL of methanol. Glacial acetic acid (150 µL) was added followed by Girard P reagent (190 mg bromide salt, 150 mg chloride salt, 0.80 mmol). The mixture was vortexed then incubated at room temperature overnight in the dark.

To remove excess reagent from the reaction mixture a recycling method was used. A 200 mg Certified Sep-Pak $C_{18}$ cartridge was pre-conditioned with methanol (6 mL), 10% methanol (6 mL) and finally 70% methanol (4 mL). The derivatization mixture from above (3.25 mL in ~70% organic) was applied to the column and allowed to flow through at ~0.25 mL/min. The column was washed with 70% methanol (1 mL) followed by 35% methanol (1 mL) and the combined eluent diluted with water (4 mL) to give a solution of ~9 mL of 35% methanol. This solution was applied to the column, collected, and combined with a column wash of 17.5% methanol (1 mL). Water (9 mL) was added to give a solution in 19 mL of 17.5% methanol which was again applied to the column. The flow-through was collected and the column washed with 10% methanol (2×6 mL). Derivatized steroids were then eluted from the column with methanol (3×1 mL, SPE2-Fr1, Fr2, Fr3) followed by absolute ethanol (1 mL, SPE2-Fr4). Cholesterol was found to be almost exclusively present in SPE2-Fr3 while oxysterols and $C_{19}$ steroid sulphates elute in SPE2-Fr1 and Fr2.

Example 4—LC-MS(MS") on the LTQ-Orbitrap

To analyse GP-tagged sterols, 120 µL from each of SPE2-Fr1 and Fr2 (240 µL in total) were diluted with 160 µL water containing 0.1% formic acid to give a final concentration of 60% methanol. For each experiment, 20 µL was injected onto the LC column and MS, $MS^2$ and $MS^3$ spectra recorded as described below.

LC was performed on a Ultimate 3000 HPLC system (Dionex, Surrey, UK) using a Hypersil GOLD revered phase column (1.9 µm particle size, 50×2.1 mm, Thermo Fisher). Mobile phase A consisted of 33.3% methanol, 16.7% acetonitrile and 0.1% formic acid. Mobile phase B consisted of 63.3% methanol, 31.7% acetonitrile and 0.1% formic acid. The chromatographic run started at 20% B for 1 min before increasing the proportion of B to 80% over 7 minutes and maintaining this for a further 5 min. The proportion of B was returned to 20% over 6 s and re-equilibration was for 3 min, 54 s to give a total run time of 17 min. The flow rate was 200 µL/min and the eluent was directed to the atmospheric pressure ionization (API) source of an LTQ-Orbitrap (either an LTQ-Orbitrap XL or Velos). The Orbitrap was calibrated externally before each analytical session and the mass accuracy was better than 5 ppm on the XL and 2 ppm on the Velos. A number of different experimental methods were used.

1. The first method consisted of a Fourier Transform (FT)-MS scan in the Orbitrap over the m/z range of 400-610 or 300-800 at 30,000 resolution (full width at half-maximum height; FWHM) with a maximum ion fill time of 500 ms. This was followed by $MS^2$ and $MS^3$ scans in the linear ion trap (LIT) with maximum ion fill times of 200 ms on the XL or 100 mS on the Velos. Three microscans were performed with the precursor ion isolation width set at 2 on the XL or 1 on the Velos, and the normalised collision energies of 30 for $MS^2$ and 35 for $MS^3$ (instrument settings). $MS^2$ was preferentially performed on [M]$^+$ ions of expected sterols based on a precursor ion inclusion list providing a minimum of 500 ion counts was reached. If a fragment ion corresponding to a neutral loss of the pyridine ring (Py) was observed in the $MS^2$ event, $MS^3$ was performed on this ion (providing a minimum of 200 ion counts was reached).

2. The second experimental method used a multiple reaction monitoring (MRM)-like approach. The Orbitrap® was scanned as described above while selected $MS^3$ transitions ($[M]^+ \to [M\text{-}Py]^+ \to$) were monitored in the LIT. Two transitions were repetitively monitored over the course of the chromatographic run.

3. The third experimental utilised the Orbitrap to monitor selected $MS^2$ transitions ($[M]^+ \to [M\text{-}Py]^+$, while the LIT recorded the fragment ions generated in the $MS^3$ transitions ($[M]^+ \to [M\text{-}Py]^+ \to$). This protocol was only exploited on the LTQ-Orbitrap Velos where the isolation width was set at 1.

Example 5—Validation of Differential and Isobaric Mass Tags

1. ESI-MS(MS/MS)

Figure 2A:
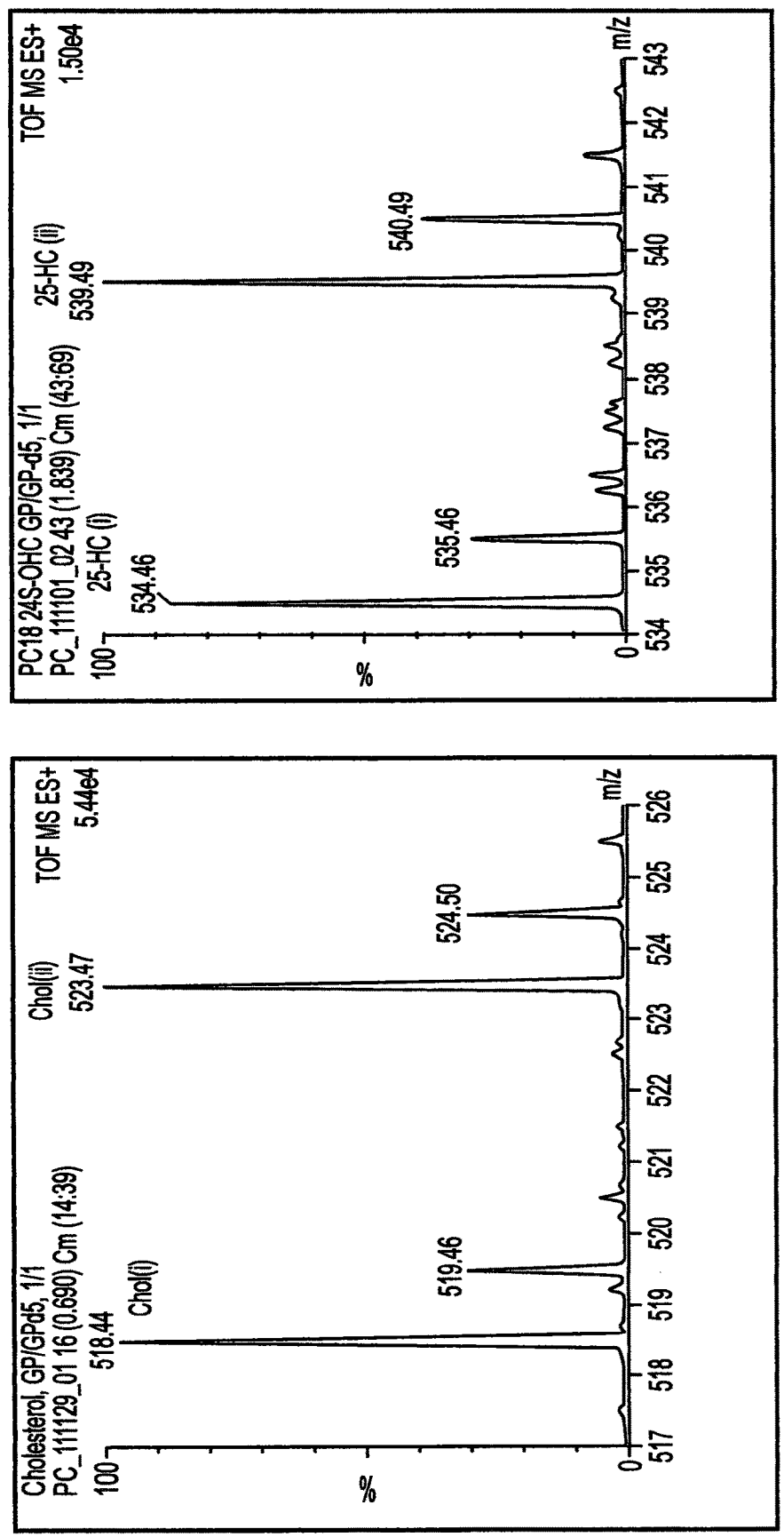
FIG. 2A illustrates the validation of quantitative charge-tags using ESI-MS recorded on a Q-TOF Ultima showing the peak intensity ratio for a 1:1 mixtures of cholesterol (Chol) and 25-hydroxycholesterol (25-HC) labelled with [$^2H_0$]-GP (i) and [$^2H_5$]-GP (ii).

For situations where separation of isomers is not a requirement, analysis can be performed by direct-infusion ESI-MS and MS/MS. Validation experiments were initially performed on the Q-TOF mass spectrometer using authentic standards at differing concentrations. Cholesterol and 25-hydroxycholesterol were used to validate the differential mass tag method. Cholesterol tagged with [$^2H_0$-GP] reagent (i of Table 1) gives an $[M]^+$ ion at m/z 518.4 and when tagged with [$^2H_5$-GP] (ii of Table 1) the $[M]^+$ ion is shifted to m/z 523.4. Similarly, the $[M]^+$ ion for 25-hydroxycholesterol is at m/z 534.4 when derivatised [$^2H_0$-GP] (i of Table 1) and at 539.4 when derivatised with [$^2H_5$-GP] (ii of Table 1). When 1:1 mixtures of sterols derivatised GP (i) and (ii) of Table 1 were analysed by ESI-MS the ratio of peak intensities for ions at 518.4 and 523.4 and for ions of 534.4 and 539.4 were essentially 1:1 (FIG. 2A). With 10:1 and 1:10 mixtures the deviation from the theoretical ratio was less than 20%. The deviation can be explained at least in-part by the inherently limited dynamic range of the Q-TOF Ultima instrument employed.

FIG. 2 illustrates the validation of quantitative charge-tags. FIG. 2(A) shows an ESI-MS recorded on Q-TOF Ultima showing the peak intensity ratio for a 1:1 mixtures of cholesterol (Chol) and 25-hydroxycholesterol (25-HC) labelled with [$^2H_0$]-GP (i of Table 1) and [$^2H_5$]-GP (ii of Table 1).

2. LC-MS(MS)$^n$ on the LTQ-Orbitrap

Figure 2B:
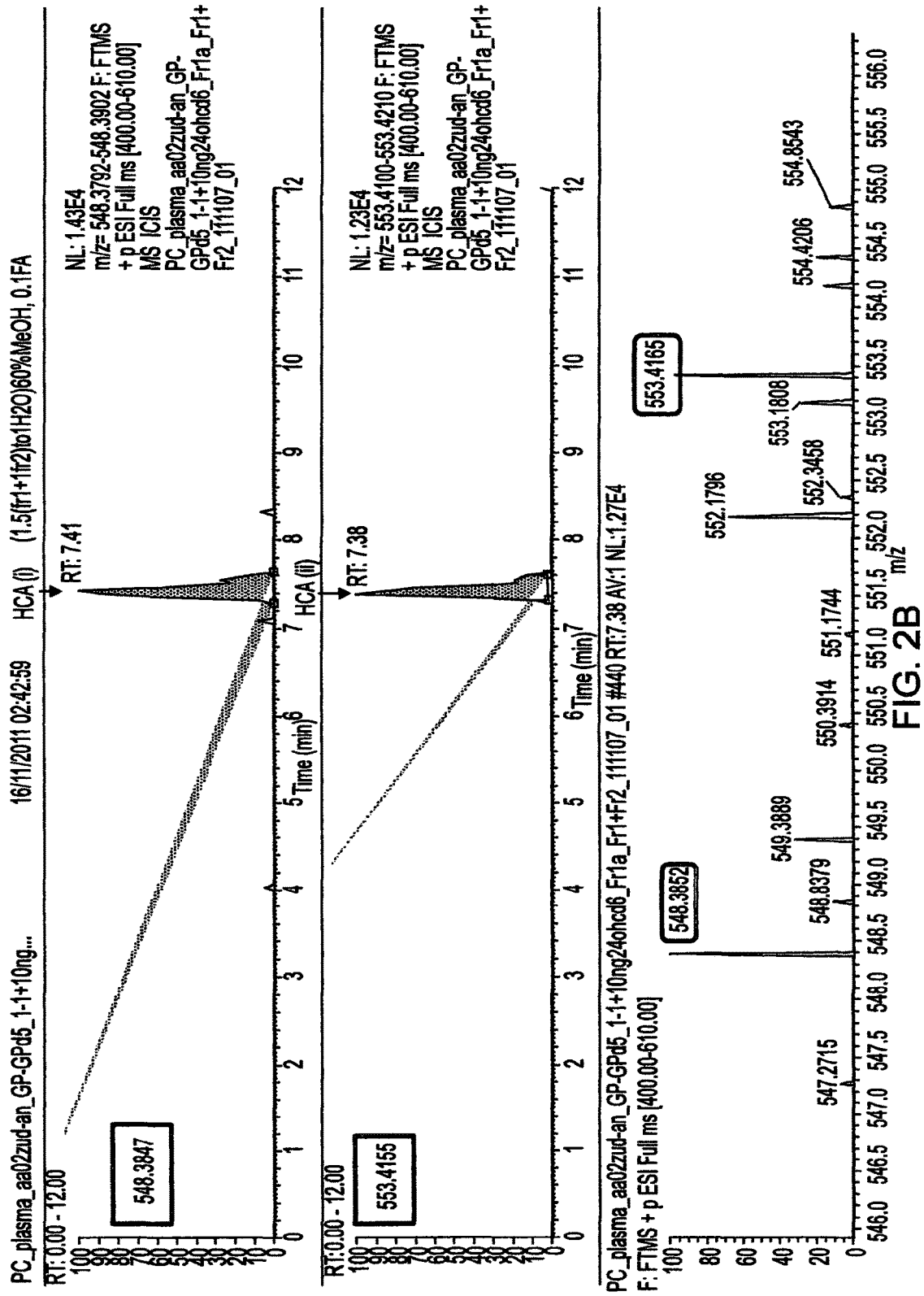
FIG. 2B illustrates the validation of quantitative charge-tags using LC-MS reconstructed-ion chromatograms (RICs) for 3β-hydroxycholest-5-enoic acid (HCA) in a 1:1 mixture of a plasma sample labelled with [$^2H_0$]-GP (i) and [$^2H_5$]-GP (ii), wherein the mass spectrum at the peak apex of 7.38 min is shown in the lower panel, and the measured ratio after normalisation with [$^2H_6$]24(R/S)hydroxycholesterol internal standard is shown in (C).
Figure 2C:
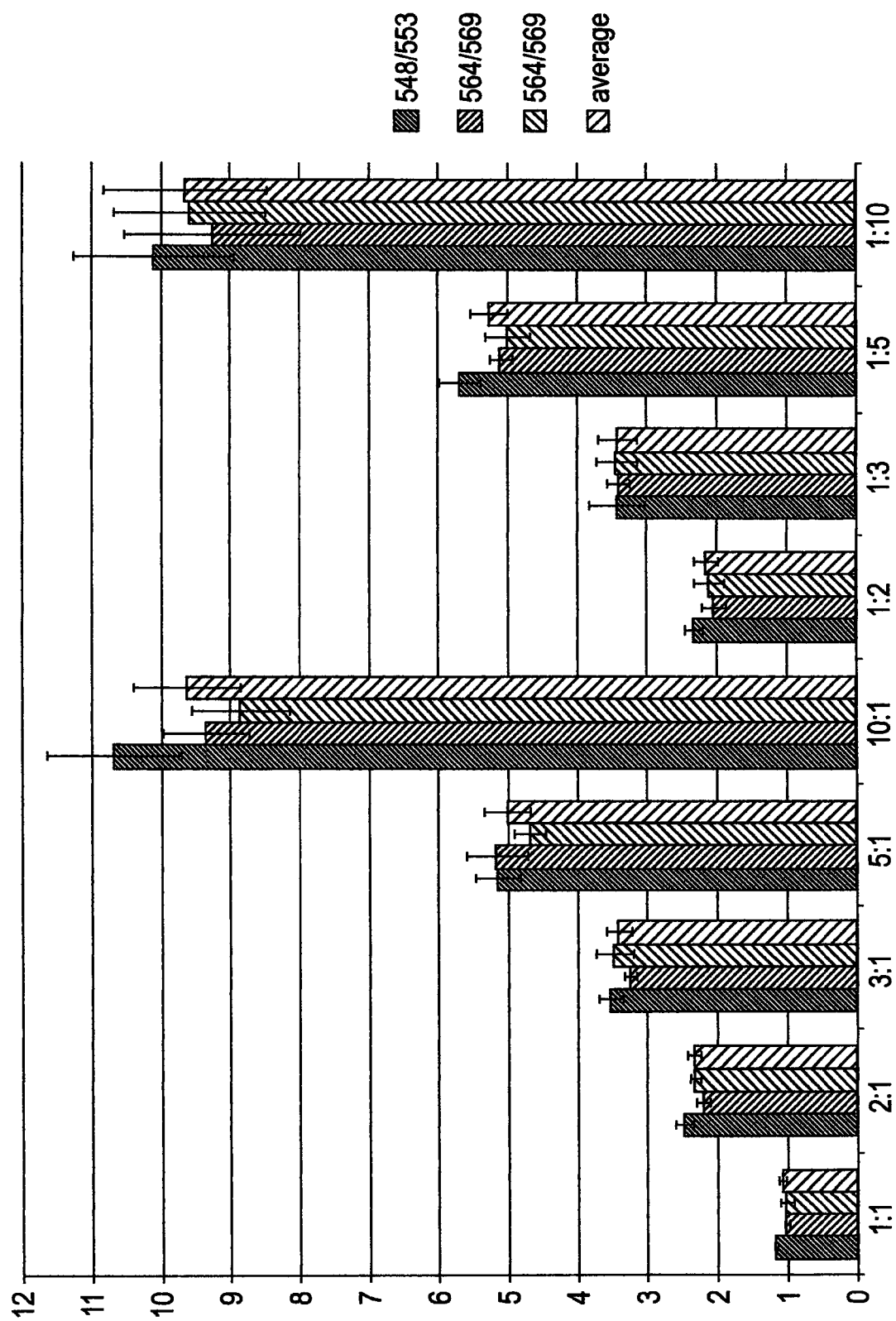
FIG. 2C illustrates the validation of quantitative charge-tags using LC-MS RIC peak intensity ratios for 3β-hydroxycholest-5-enoic acid (548/553) and 3β,7α-dihydroxycholest-5-enoic plus 7α-hydroxy-3-oxocholest-5-enoic acids (564/569) in mixtures of plasma samples labelled with [$^2H_0$]-GP (i) and [$^2H_5$]-GP (ii).
Figure 6:
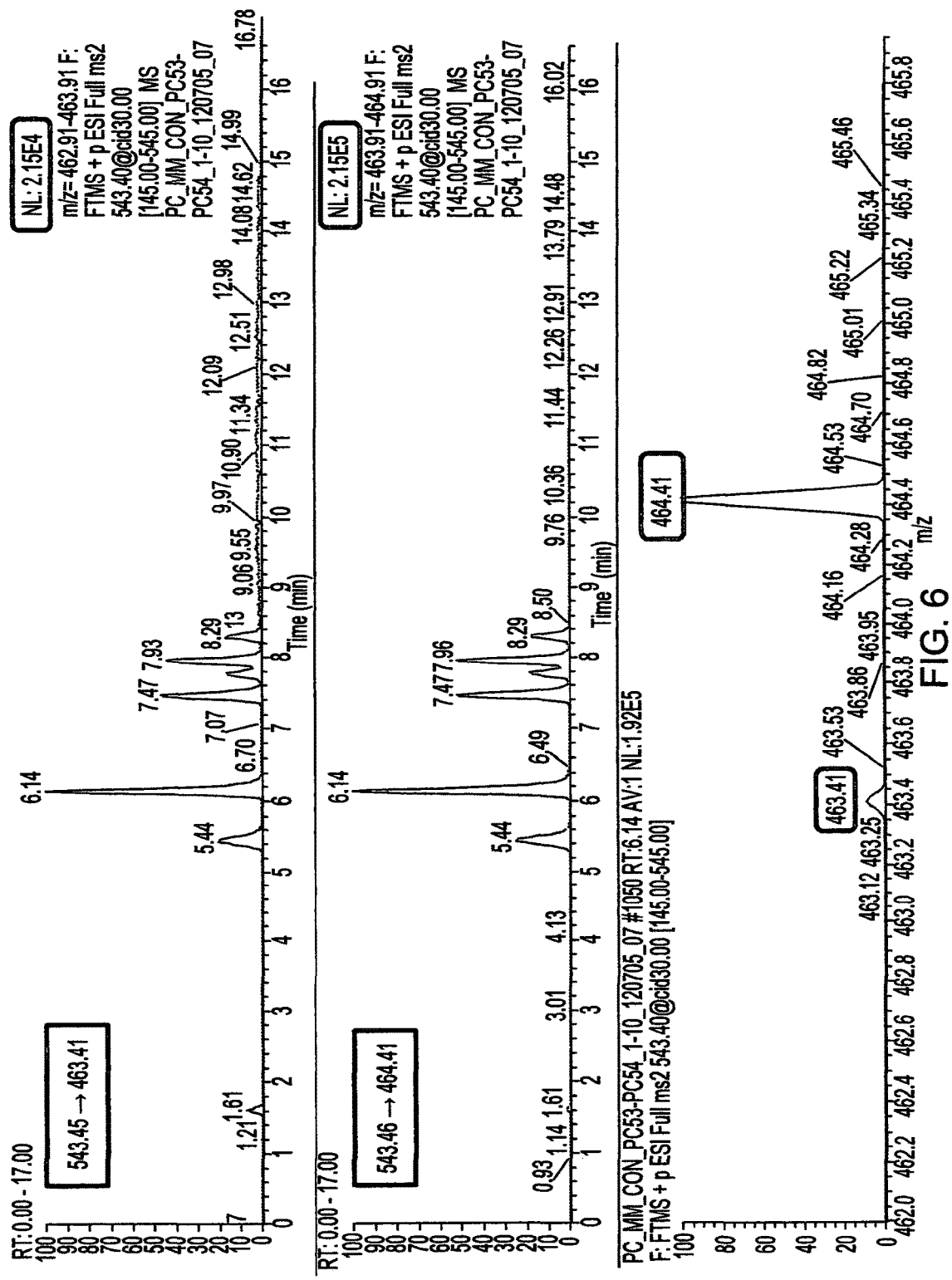
FIG. 6 illustrates the validation of isobaric mass tags using a similar method to that used for FIG. 2 and a 1:10 ratio of cholesterol (Chol) and 25-hydroxycholesterol (25-HC) labelled with [$^2$H$_0$]-GP (i of Table 1) and [$^2$H$_5$]-GP (ii of Table 1).

To validate the concept of differential mass tags for steroid analysis by LC-MS, aliquots of control plasma were analysed on the LTQ-Orbitrap at volume ratios 1:1, 2:1, 3:1 5:1, 10:1, 1:2, 1:3, 1:5 and 1:10 after labelling with [$^2H_0$]-GP (i of Table 1) and [$^2H_5$]-GP (ii of Table 1) reagents, respectively (FIGS. 2B & C). As is shown in FIG. 2C the measured analyte ratios are in good agreement with the theoretical values. To correct for any sample handling errors prior to LC-MS analysis, the common internal standard [26,26,26, 27,27,27-$^2H_6$]24(R/S)-hydroxycholesterol was used throughout. Similar experiments performed with isobaric mass tags which also gave satisfactory ratios over the same concentration range utilizing the $MS^2$ $[M]^+ \to [M\text{-}Py]^+$ and $MS^3$ $[M]^+ \to [M\text{-}Py]^+ \to$ transitions. A 1:10 ratio is illustrated in FIG. 6).

Example 6—Simultaneous Quantification of 3-Oxo- and 3β-Hydroxy-Steroids

Figure 3A:
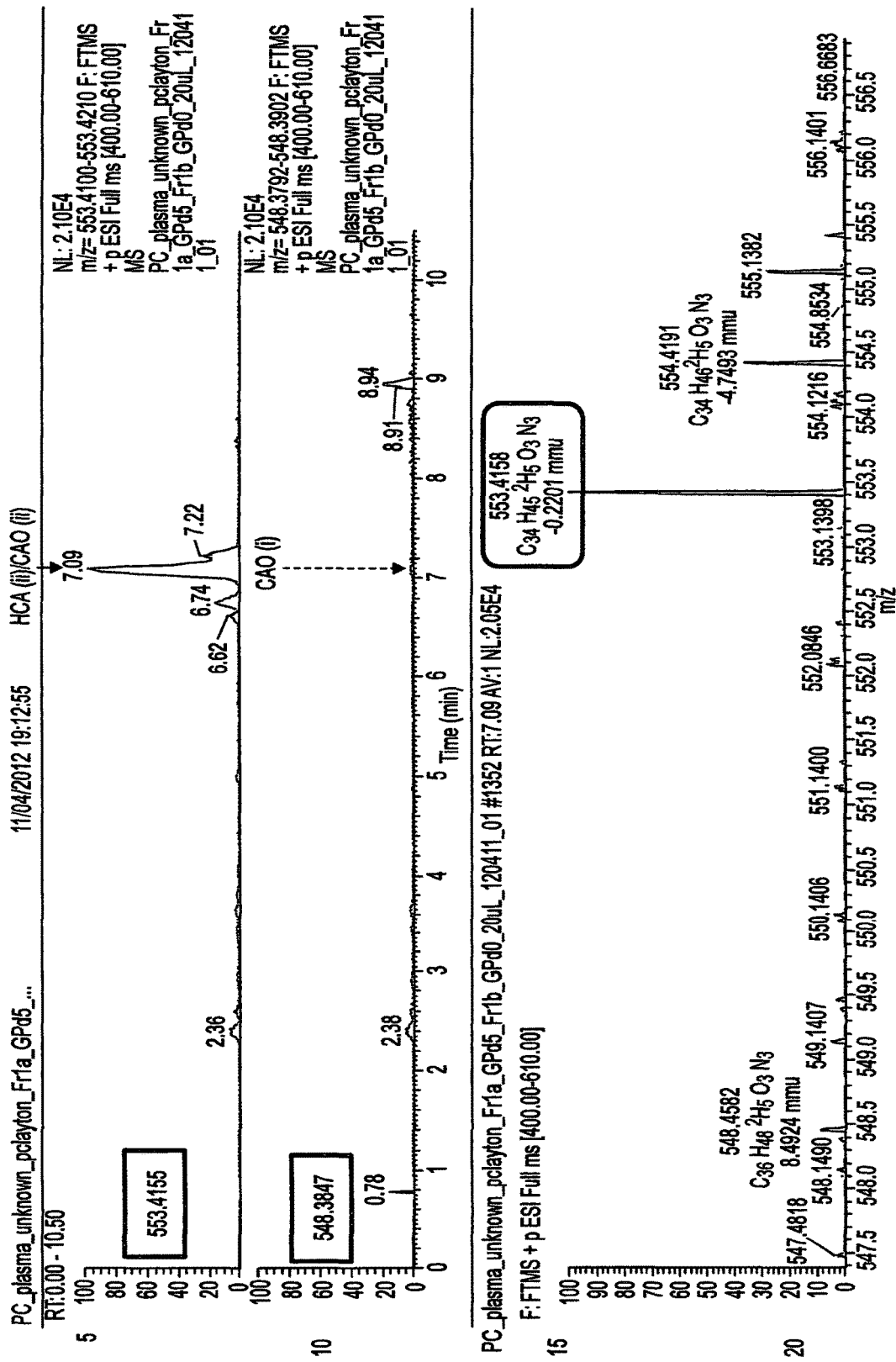
FIG. 3A shows an LC-MS analysis of a plasma sample from a child with a neurological disease of unknown aetiology, with RIC of m/z 553.4155 corresponding to [M]$^+$ ions of 3β-hydroxycholest-5-enoic (HCA) and 3-oxocholest-4-enoic (CAO) acids derivatised with [$^2H_5$]-GP (ii) following cholesterol oxidase treatment, and of m/z 548.3847 corresponding to [M]$^+$ ions of 3-oxocholest-4-enoic acid derivatised with [$^2H_0$]-GP (i) in the absence of cholesterol oxidase treatment. The chromatograms are plotted on an identical intensity scale. The absence of an appropriate peak in the RIC of m/z 548.3847 indicates that no 3-oxocholest-4-enoic acid is present in plasma. The lower panel shows the mass spectrum recorded at the peak apex of 7.09 min.
Figure 3B:
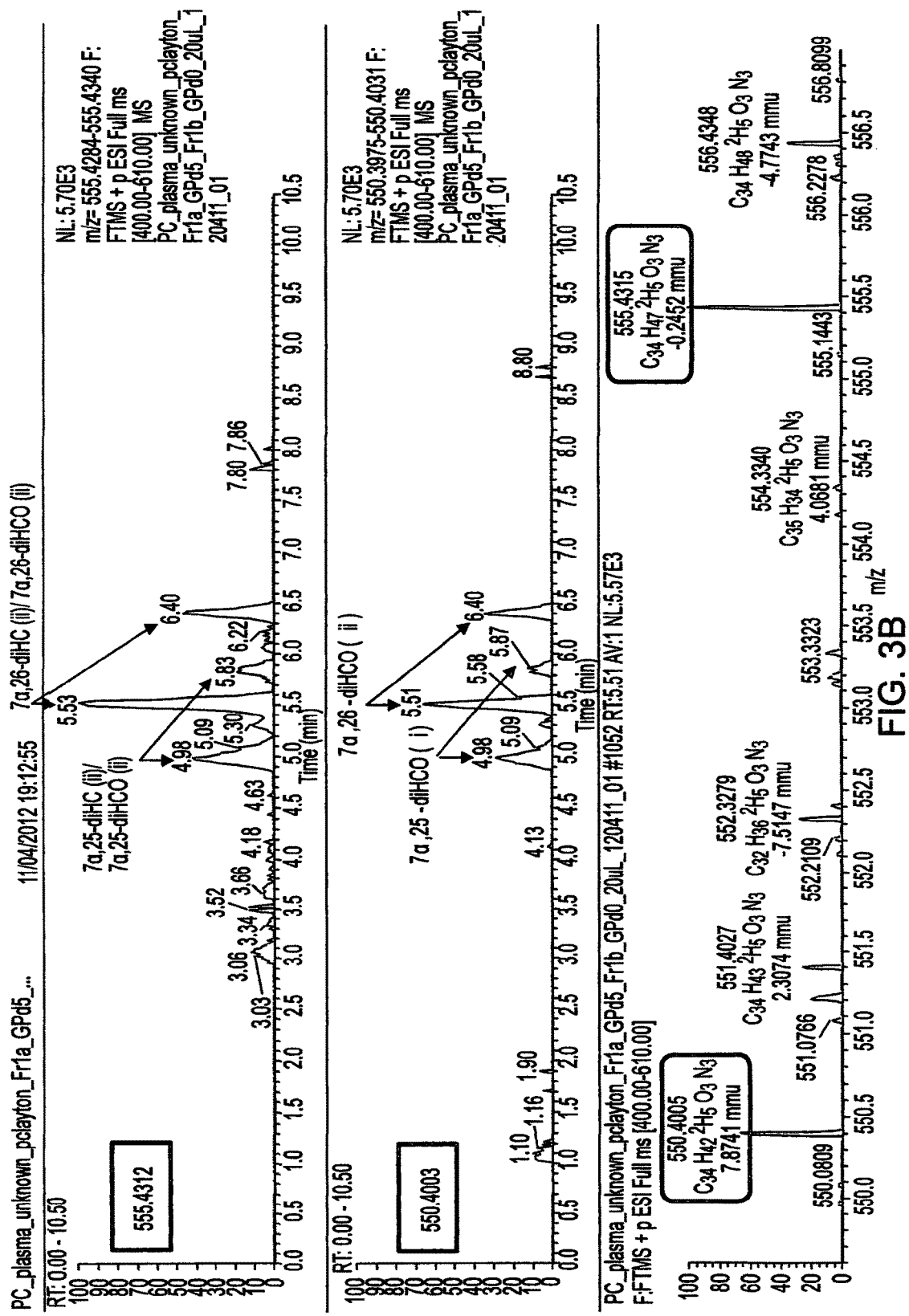
FIG. 3B shows an LC-MS analysis of a plasma sample from a child with a neurological disease of unknown aetiology, with RIC of m/z 555.4312 corresponding to [M]$^+$ ions of dihydroxycholesterols (diHC) and dihydroxycholestenones (diHCO) derivatised with [$^2H_5$]-GP (ii) following cholesterol oxidase treatment, and of m/z 550.4003 corresponding to [M]$^+$ ions of dihydroxycholestenones derivatised with [$^2H_0$]-GP (i) in the absence of cholesterol oxidase treatment. The presence of appropriate peaks in the RIC of m/z 550.4003 indicates that dihydroxycholestenones are present in the sample. The enhanced abundance of peaks in the RIC of m/z 555.4312 over m/z 550.4003 indicates that dihydroxycholesterols are also present. The chromatograms are plotted on an identical intensity scale. The lower panel shows the mass spectrum recorded at the peak apex of 5.51 min. Both the 7α,25- and 7α,26-dihydroycholesterol/dihydroxycholesten-3-one isomers appear as syn and anti conformers following derivatisation.
Figure 3C:
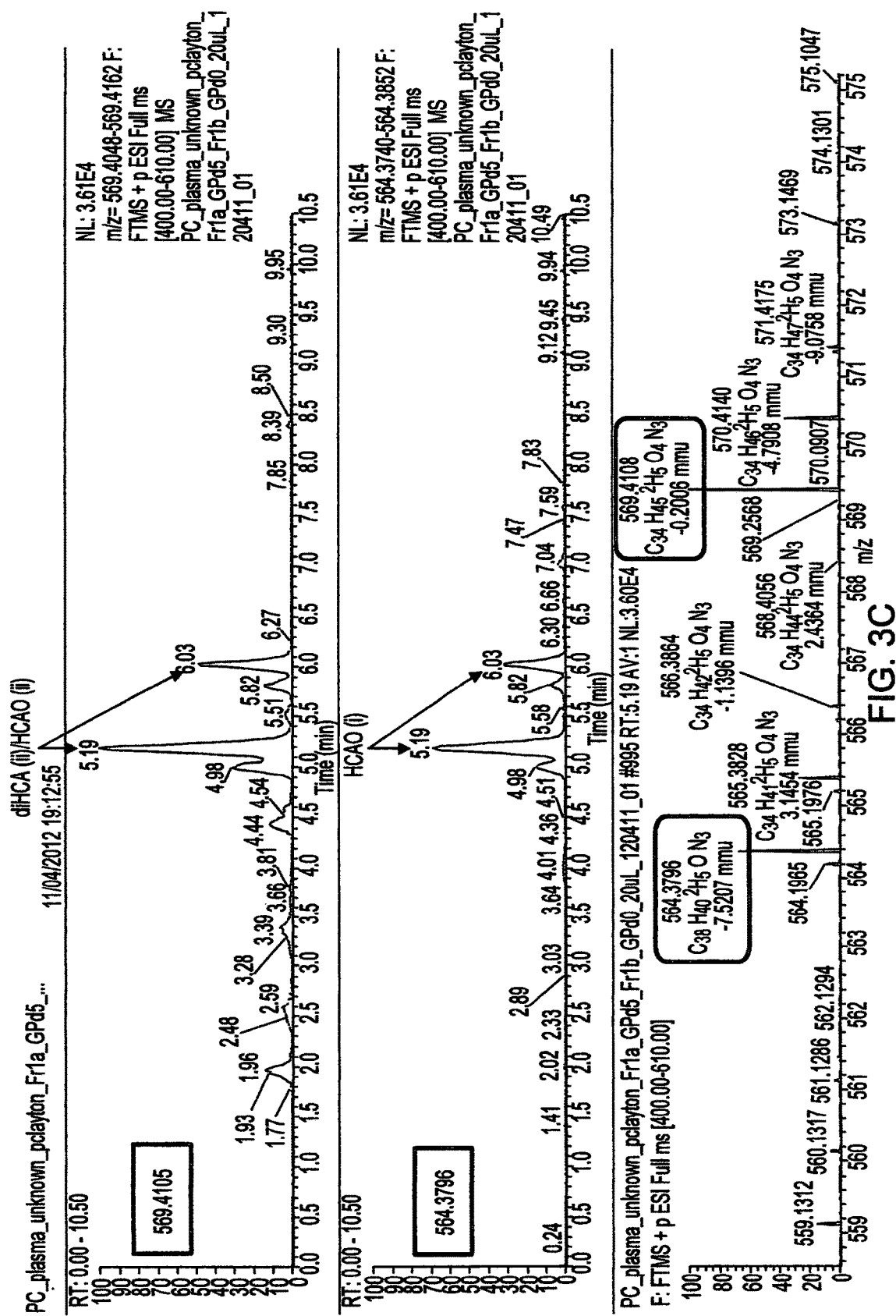
FIG. 3C shows an LC-MS analysis of a plasma sample from a child with a neurological disease of unknown aetiology, with RIC of m/z 569.4105 corresponding to [M]$^+$ ions of dihydroxycholestenoic (diHCA) and hydroxyoxocholestenoic (HCAO) acids derivatised with [$^2H_5$]-GP (ii) following cholesterol oxidase treatment, and of m/z 564.3796 corresponding to [M]$^+$ ions of hydroxyoxocholestenoic acids derivatised with [$^2H_0$]-GP (i) in the absence of cholesterol oxidase treatment. The chromatograms are plotted on an identical intensity scale. The lower panel shows the mass spectrum recorded at the peak apex of 5.19 min. Both the 3β,7α-dihydroycholest-5-enoic/7α-hydroxy-3-oxocholesten-4-enoic acids appear as syn and anti conformers following derivatisation.

Quantitative charge-tags can be used to differentiate between molecules naturally possessing an oxo group and those oxidized by e.g. cholesterol oxidase, to contain one. This allows the profiling of all oxo and 3β-hydroxy steroids in a single analysis as set out in Table S1. Here we illustrate this with infant plasma. Two identical aliquots of infant plasma were worked up in parallel with or without enzymatic oxidation. The oxidised sample was derivatised with [$^2H_5$]-GP (ii of Table 1), while the non-oxidised sample was derivatised with [$^2H_0$]-GP (i of Table 1). The samples were analysed by LC-MS using the LTQ-Orbitrap. By plotting reconstructed ion chromatograms (RICs) for molecules derivatised with [$^2H_5$]-GP (ii) (following cholesterol oxidase treatment) and [$^2H_0$]-GP (i) (in the absence of cholesterol oxidase) the quantities of 3-oxo compounds were revealed by the intensity of [$^2H_0$]-GP (i) labelled analytes and the quantities of 3β-hydroxy compounds by the difference in intensity of [$^2H_5$]-GP (ii) and [$^2H_0$]-GP (i) labelled analytes. From FIG. 3A it is clear that there is essentially no endogenous 3-oxocholest-4-enoic acid, but a high level of the cholesterol oxidase substrate 3β-hydroxycholest-5-enoic acid. The situation is different for 7α,25- and 7α,26-dihydroxycholesterols which are accompanied in plasma by their down-stream metabolites 7α,25- and 7α,26-dihydroxycholest-4-en-3-ones, and also for 3β,7α-dihydroxycholest-5-enoic acid and its metabolite 7α-hydroxy-3-oxocholest-4-enoic acid (FIGS. 3B & 3C). Table S1 contains data for all the metabolites detected in infant and pooled adult plasma. Table S1 shows steroids, oxysterols and cholestenoic acids detected by LC-ESI-MS$^n$ in plasma following SPE and charge-tagging with GP-hydrazine. In the absence of authentic standards presumptive identifications based on exact mass, MS$^n$ spectra and retention time are given. Control values are given in parenthesis.

TABLE S1

Steroids, Oxysterols and Cholestenoic Acids in Human Plasma.

| | | After cholesterol oxidase and GP-tagging | | Originating structure | | | |
|---|---|---|---|---|---|---|---|
| Met ID | Mass | Formula | Sterol Systematic name | Sterol Systematic name (common name) | RT | AS | ng/mL |
| | 502.237 | $C_{26}H_{36}N_3O_5S^+$ | 3β-Hydroxyandrost-5-en-17-one 3-sulphate 17-GP | 3β-Hydroxyandrost-5-en-17-one 3-sulphate (Dehydroepiandrosterone) | 0.8 | Y | (264.0) |
| | 504.2527 | $C_{26}H_{38}N_3O_5S^+$ | 3-Hydroxyandrostan-17-one 3-sulphate 17-GP | 3-Hydroxyandrostan-17-one 3-sulphate | 0.83 | N | (36.9) |
| | 504.2527 | $C_{26}H_{38}N_3O_5S^+$ | 3-Hydroxyandrostan-17-one 3-sulphate 17-GP | 3-Hydroxyandrostan-17-one 3-sulphate | 1.02 | N | (154.3) |
| | 518.2319 | $C_{26}H_{36}N_3O_6S^+$ | 3β,x-Dihydroxyandrost-5-en-17-one 3-sulphate 17-GP | 3β,x-Dihydroxyandrost-5-en-17-one 3-sulphate | | N | (5.9) |
| | 600.3279 | $C_{32}H_{46}N_3O_8^+$ | 3-Hydroxyandrostan-17-one 3-glucuronide 17-GP | 3-Hydroxyandrostan-17-one 3-glucuronide | 1.05 | N | (22.8) |
| | 516.3948 | $C_{34}H_{50}N_3O^+$ | Cholesta-4,24-dien-3-one 3-GP | Cholesta-5,24-dien-3β-ol (Desmosterol) | 10.83 | Y | |

TABLE S1-continued

Steroids, Oxysterols and Cholestenoic Acids in Human Plasma.

| | | After cholesterol oxidase and GP-tagging | | Originating structure | | | |
|---|---|---|---|---|---|---|---|
| Met ID | Mass | Formula | Sterol Systematic name | Sterol Systematic name (common name) | RT | AS | ng/mL |
| | 516.3948 | $C_{34}H_{50}N_3O^+$ | Cholesta-4,7-dien-3-one 3-GP | Cholesta-5,7-dien-3β-ol (7-Dehydrocholesterol) | 12.07 | Y | |
| | 518.4105 | $C_{34}H_{52}N_3O^+$ | Cholest-4-en-3-one 3-GP | Cholest-5-en-3β-ol (Cholesterol) | 11.7 | Y | |
| | 520.4261 | $C_{34}H_{54}N_3O^+$ | 5α-Cholestan-3-one 3-GP | 5α-Cholestan-3β-ol (Cholestanol) | | Y | |
| | 504.3221 | $C_{31}H_{42}N_3O_3^+$ | 3-Oxochol-4,6-dien-24-oic acid 3-GP | 3-Oxochol-4,6-dien-24-oic acid | 3.45 | N | (1.4) 38.46 |
| | 504.3221 | $C_{31}H_{42}N_3O_3^+$ | 3-Oxochol-4,6-dien-24-oic acid 3-GP | 3β-hydroxychol-5,7-dien-24-oic acid | 3.45 | N | (1.0) 16.08 |
| | 506.3377 | $C_{31}H_{44}N_3O_3^+$ | 3-Oxochol-4-en-24-oic acid 3-GP | 3-Oxochol-4-en-24-oic acid | 4.57 | Y | (ND) 6.56 |
| | 506.3377 | $C_{31}H_{44}N_3O_3^+$ | 3-Oxochol-4-en-24-oic acid 3-GP | 3β-hydroxychol-5-en-24-oic acid | 4.57 | Y | (4.5) 355.29 |
| | 522.3326 | $C_{31}H_{44}N_3O_4^+$ | 7α-Hydroxy-3-oxochol-4-en-24-oic acid 3-GP | 7α-Hydroxy-3-oxochol-4-en-24-oic acid | 2.18 | Y | (3.9) 25.57 |
| | 522.3326 | $C_{31}H_{44}N_3O_4^+$ | 7α-Hydroxy-3-oxochol-4-en-24-oic acid 3-GP | 3β,7α-Dihydroxychol-5-en-24-oic acid | 2.18 | Y | (9.2) 7.64 |
| | 532.3898 | $C_{34}H_{50}N_3O_2^+$ | Cholest-4-ene-3,24-dione 3-GP | Cholest-4-ene-3,24-dione | 7.91 | Y | (3.2) 0.82 |
| | 532.3898 | $C_{34}H_{50}N_3O_2^+$ | Cholest-4-ene-3,24-dione 3-GP | 3β-Hydroxycholest-5-en-24-one | 7.91 | Y | (ND) 45.05 |
| | 534.4054 | $C_{34}H_{52}N_3O_2^+$ | 24S-Hydroxycholest-4-en-3-one 3-GP | Cholest-5-ene-3β,24S-diol (24S-Hydroxycholesterol) | 7.60 | Y | (6.5) 172.60 |
| | 534.4054 | $C_{34}H_{52}N_3O_2^+$ | 25-Hydroxycholest-4-en-3-one 3-GP | Cholest-5-ene-3β,25-diol (25-Hydroxycholesterol) | 7.91 | Y | (<5) 398.41 |
| | 534.4054 | $C_{34}H_{52}N_3O_2^+$ | 26-Hydroxycholest-4-en-3-one 3-GP | Cholest-5-ene-3β,26-diol ((25R),26-Hydroxycholesterol) | 8.14 | Y | (17.7) 1743.20 |
| | 534.4054 | $C_{34}H_{52}N_3O_2^+$ | 7β-Hydroxycholest-4-en-3-one 3-GP | Cholest-5-ene-3β,7β-diol (7β-Hydroxycholesterol) | 9.84 | Y | (<1) 21.00 |
| | 534.4054 | $C_{34}H_{52}N_3O_2^+$ | 3β-Hydroxycholest-5-en-7-one 7-GP | 3β-Hydroxycholest-5-en-7-one (7-Oxocholesterol) | 9.93 | Y | (<1) 11.35 |
| | 534.4054 | $C_{34}H_{52}N_3O_2^+$ | 7α-Hydroxycholest-4-en-3-one 3-GP | Cholest-5-ene-3β,7α-diol (7α-Hydroxycholesterol) | 10.39 | Y | (<1) 10.21 |
| | 546.3690 | $C_{34}H_{48}N_3O_3^+$ | 3-Oxocholest-4,x-dien-26-oic acid 3-GP | 3-Oxocholest-4,x-dien-26-oic acid 3 | 7.35 | N | (21.8) 15.55 |
| | 546.3690 | $C_{34}H_{48}N_3O_3^+$ | 3-Oxocholest-4,x-dien-26-oic acid 3-GP | 3β-Hydroxycholest-5,x-dien-26-oic acid | 7.35 | N | (ND) 150.83 |
| | 548.3847 | $C_{34}H_{50}N_3O_3^+$ | x-Hydroxycholest-4-en-3,y-dione 3-GP | 3β,x-Dihydroxycholest-5-en-y-one | 6.87 | N | (5.3) (ND) |
| | 548.3847 | $C_{34}H_{50}N_3O_3^+$ | 3-Oxocholest-4-en-26-oic acid 3-GP | 3-Oxocholest-4-en-26-oic acid | 7.84 | Y | (ND) 96.40 |
| | 548.3847 | $C_{34}H_{50}N_3O_3^+$ | 3-Oxocholest-4-en-26-oic acid 3-GP | 3β-Hydroxycholest-5-en-26-oic acid | 7.84 | Y | (118.4) 4217.53 |
| | 550.4003 | $C_{34}H_{52}N_3O_3^+$ | x,y-Dihydroxycholest-4-en-3-one 3-GP | Cholest-5-ene-3β,x,y-triol | 3.69 | N | (ND) 105.65 |
| | 550.4003 | $C_{34}H_{52}N_3O_3^+$ | x,y-Dihydroxycholest-4-en-3-one 3-GP | Cholest-5-ene-3β,x,y-triol | 3.93 | N | (ND) 55.79 |
| | 550.4003 | $C_{34}H_{52}N_3O_3^+$ | 24,25-Dihydroxycholest-4-en-3-one 3-GP | Cholest-5-ene-3β,24,25-triol | 5.13 | Y | (ND) 409.27 |
| | 550.4003 | $C_{34}H_{52}N_3O_3^+$ | 7α,25-Dihydroxycholest-4-en-3-one 3-GP | 7α,25-Dihydroxycholest-4-en-3-one | 5.14 | Y | (3.1) ND |
| | 550.4003 | $C_{34}H_{52}N_3O_3^+$ | 7α,26-Dihydroxycholest-4-en-3-one 3-GP | 7α,26-Dihydroxycholest-4-en-3-one | 5.66 | Y | (9.8) |
| | 550.4003 | $C_{34}H_{52}N_3O_3^+$ | 7α,12α-Dihydroxycholest-4-en-3-one 3-GP | 7α,12α-Dihydroxycholest-4-en-3-one | 8.95 | Y | |
| | 550.4003 | $C_{34}H_{52}N_3O_3^+$ | 7α,12α-Dihydroxycholest-4-en-3-one 3-GP | Cholest-5-en-3β,7α,12α-triol | 8.95 | Y | |
| | 564.3796 | $C_{34}H_{50}N_3O_4^+$ | x-Hydroxy-3-oxocholest-4-en-26-oic acid 3-GP/x,y-dihydroxycholest-4-en-3,z-dione 3GP | 3β,x-Dihydroxycholest-5-en-26-oic acid//3β,x,y-trihydroxycholest-5-en-z-one | 2.32 | N | (13.8) 9.93 |
| | 564.3796 | $C_{34}H_{50}N_3O_4^+$ | x-Hydroxy-3-oxocholest-4-en-26-oic acid 3-GP/x,y-dihydroxycholest-4-en-3,z-dione 3GP | 3β,x-Dihydroxycholest-5-en-26-oic acid//3β,x,y-trihydroxycholest-5-en-z-one | 2.72 | N | (3.8) ND |
| | 564.3796 | $C_{34}H_{50}N_3O_4^+$ | 7β-Hydroxy-3-oxocholest-4-en-26-oic acid 3-GP | 3β,7β-Dihydroxycholest-5-en-26-oic acid | 3.55 | Y | (15.2) ND |
| | 564.3796 | $C_{34}H_{50}N_3O_4^+$ | x-Hydroxy-3-oxocholest-4-en-26-oic acid 3-GP/x,y-dihydroxycholest-4-en-3,z-dione | x-Hydroxy-3-oxocholest-4-en-26-oic acid/x,y-dihydroxycholest-4-en-3,z-dione | 4.77 | N | (ND) 8.29 |
| | 564.3796 | $C_{34}H_{50}N_3O_4^+$ | x-Hydroxy-3-oxocholest-4-en-26-oic acid 3-GP/x,y-dihydroxycholest-4-en-3,z-dione | 3β,x-Dihydroxycholest-5-en-26-oic acid//3β,x,y-trihydroxycholest-5-en-z-one | 4.77 | N | (ND) 36.72 |
| | 564.3796 | $C_{34}H_{50}N_3O_4^+$ | x-Hydroxy-3-oxocholest-4-en-26-oic acid 3-GP/x,y-dihydroxycholest-4-en-3,z-dione | 3β,x-Dihydroxycholest-5-en-26-oic acid//3β,x,y-trihydroxycholest-5-en-z-one | 5.27 | N | (ND) 21.73 |

TABLE S1-continued

Steroids, Oxysterols and Cholestenoic Acids in Human Plasma.

| | | After cholesterol oxidase and GP-tagging | | Originating structure | | | |
|---|---|---|---|---|---|---|---|
| Met ID | Mass | Formula | Sterol Systematic name | Sterol Systematic name (common name) | RT | AS | ng/mL |
| | 564.3796 | $C_{34}H_{50}N_3O_4^+$ | x-Hydroxy-3-oxocholest-4-en-26-oic acid 3-GP/x,y-dihydroxycholest-4-en-3,z-dione | 3β,x-Dihydroxycholest-5-en-26-oic acid//3β,x,y-trihydroxycholest-5-en-z-one | 4.6 | N | (18.9) ND |
| | 564.3796 | $C_{34}H_{50}N_3O_4^+$ | 7α-Hydroxy-3-oxocholest-4-en-26-oic acid 3-GP | 7α-Hydroxy-3-oxocholest-4-en-26-oic acid | 6.11 | Y | (149.4) 11.23 |
| | 564.3796 | $C_{34}H_{50}N_3O_4^+$ | 7α-Hydroxy-3-oxocholest-4-en-26-oic acid 3-GP | 3β,7α-Dihydroxycholest-5-en-26-oic acid | 6.11 | Y | (53.7) ND |
| | 566.3952 | $C_{34}H_{52}N_3O_4^+$ | 7α,12α,x-Trihydroxycholest-4-en-3-one 3-GP | 7α,12α,x-Trihydroxycholest-4-en-3-one | 3.87 | N | |
| | 580.3745 | $C_{34}H_{50}N_3O_5^+$ | 7α,x-Dihydroxy-3-oxocholest-4-enoic acid 3-GP | 7α,x-Dihydroxy-3-oxocholest-4-enoic acid | 2.16 | N | (1.7) ND |
| | 580.3745 | $C_{34}H_{50}N_3O_5^+$ | 7α,y-Dihydroxy-3-oxocholest-4-enoic acid 3-GP | 7α,y-Dihydroxy-3-oxocholest-4-enoic acid | 3.6 | N | (1.19) |
| | 612.3466 | $C_{34}H_{50}N_3O_5S^+$ | x-Hydroxycholest-4,y-dien-3-one 3-PG sulphate | x-Hydroxycholest-4,y-dien-3-one sulphate | 5.62 | N | (ND) 33.14 |
| | 612.3466 | $C_{34}H_{50}N_3O_5S^+$ | x-Hydroxycholest-4,y-dien-3-one 3GP sulphate | Cholest-5,y-diene-3β,x-diol sulphate | 5.62 | N | (ND) 22.20 |
| | 614.3622 | $C_{34}H_{52}N_3O_5S^+$ | x-Hydroxycholest-4-en-3-one 3GP sulphate | Cholest-5-ene-3β,x-diol sulphate | 6.88 | N | (ND) 1496.30 |
| | 614.3622 | $C_{34}H_{52}N_3O_5S^+$ | x-Hydroxycholest-4-en-3-one 3GP sulphate | Cholest-5-ene-3β,x-diol sulphate | 7.4 | N | (ND) 390.04 |
| | 630.3571 | $C_{34}H_{52}N_3O_6S^+$ | x,y-Dihydroxycholest-4-en-3-one 3GP sulphate | Cholest-5-ene-3β,x,y-triol sulphate | 3.96 | N | (ND) 28.47 |
| | 710.44 | $C_{40}H_{60}N_3O_8^+$ | x-Hydroxycholest-4-en-3-one 3GP GlcA | Cholest-5-ene-3β,x-diol GlcA | 6.47 | N | (ND) 173.92 |

RT = Retention time/min; AS = Authentic standard, Y = Yes, N = No; ND = Not detected;

Example 7—Diagnosis of Oxysterol 7α-hydroxylase Deficiency, CTX and SLOS

The method of Example 6 was essentially repeated, but with a patient and control sample both treated with cholesterol oxidase prior to derivatisation to illustrate the use of the methods of the invention to diagnose oxysterol 7α-hydroxylase deficiency, CTX and SLOS.

Figure 4A:
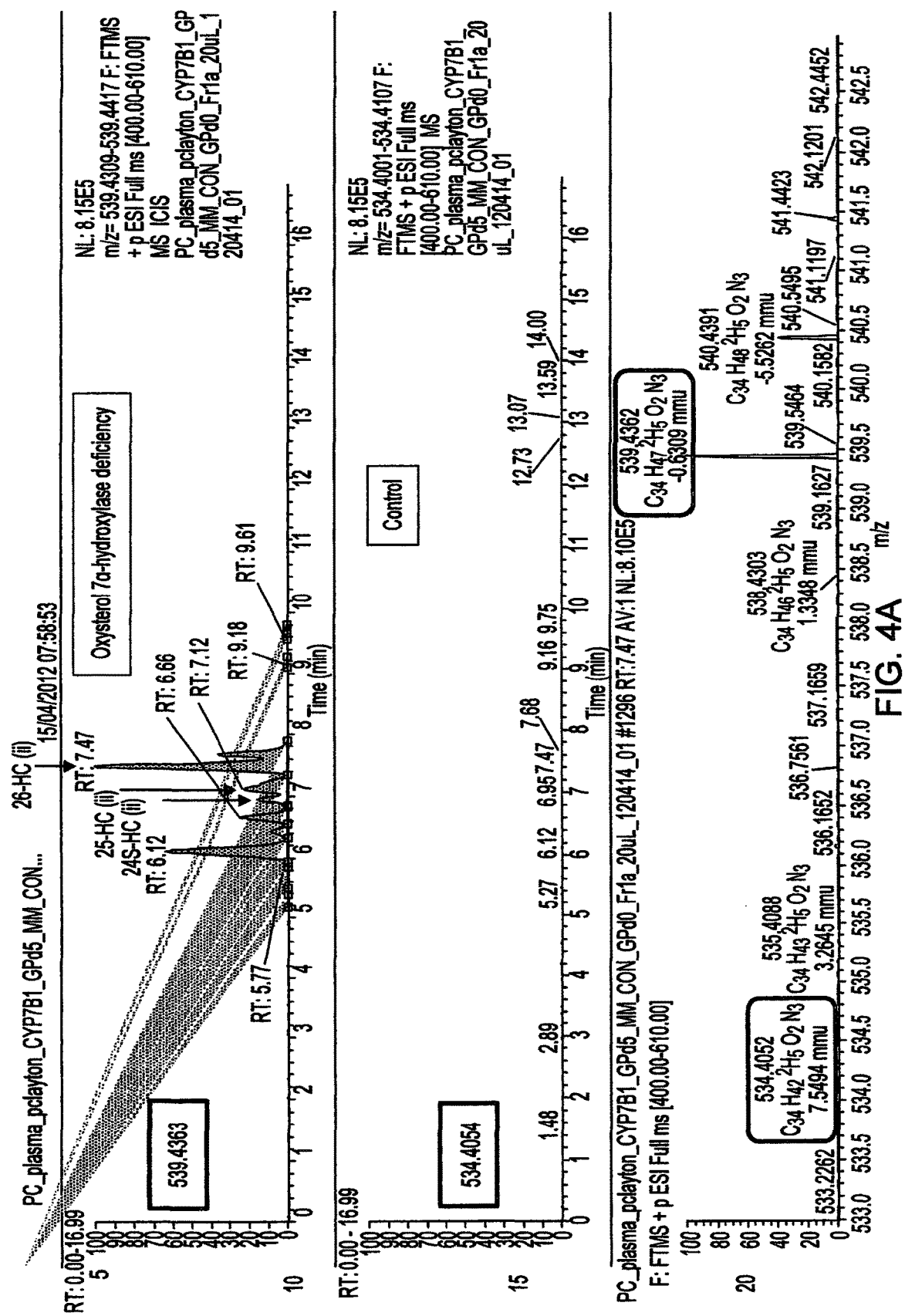
FIG. 4A depicts characterisation of inborn errors of metabolism from patient plasma, with RIC of 539.4363 and 534.4054 corresponding to [M]$^+$ ions of monohydroxycholesterols (HC) labelled with [$^2H_5$]-GP (ii) from patient plasma and with [$^2H_0$]-GP (i) from control plasma. Both chromatograms are plotted on an identical intensity scale. The lower panels are mass spectra recorded at peak apex of 7.47 min and 7.16 min, respectively. The chromatograms define the inborn error of metabolism to be oxysterol 7α-hydroxylase deficiency.
Figure 4B:
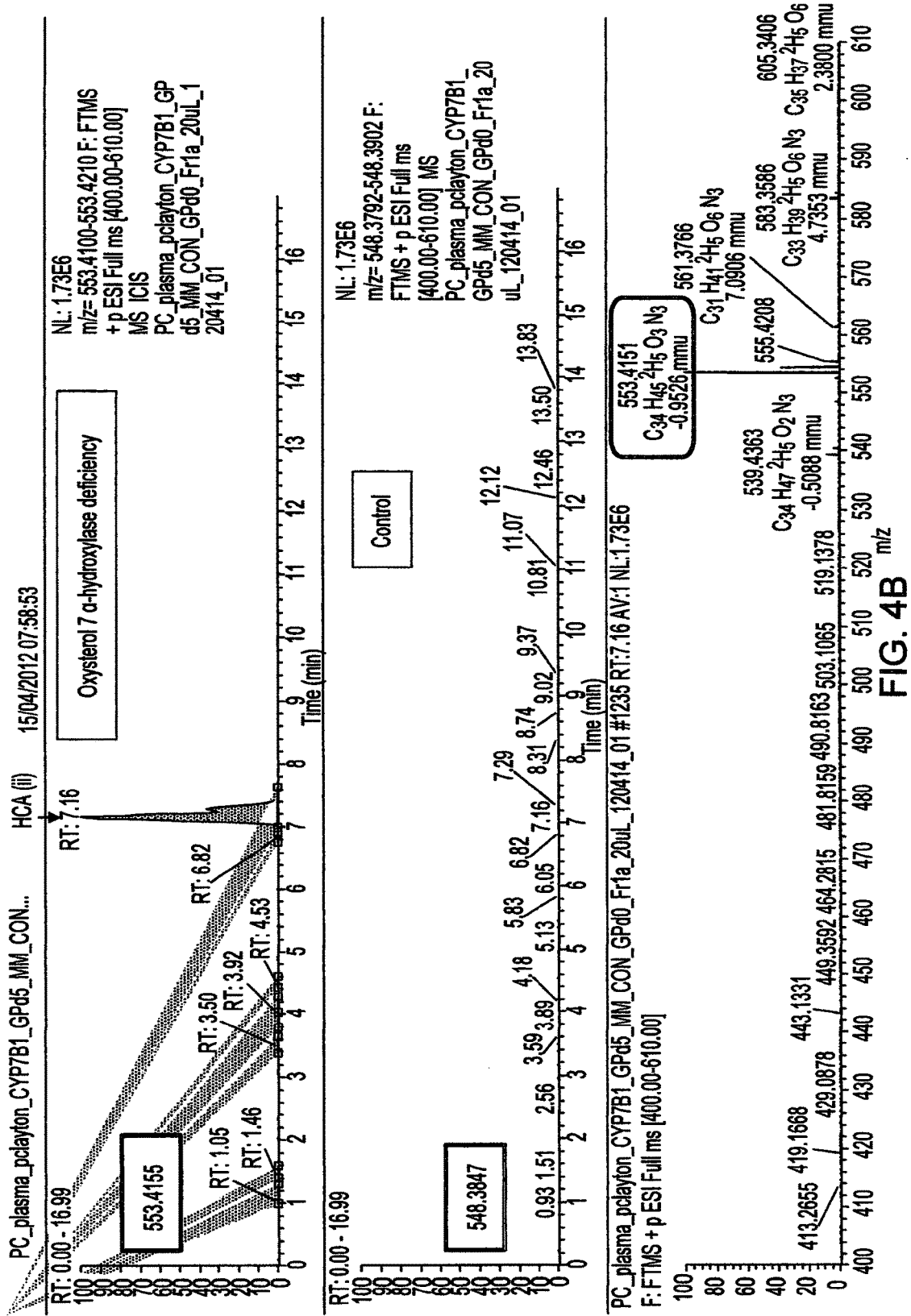
FIG. 4B depicts characterisation of inborn errors of metabolism from patient plasma, with RIC of 553.4155 and 548.3847 corresponding to [M]$^+$ ions of 3β-hydroxycholest-5-enoic acid (HCA) labelled with [$^2$H$_5$]-GP (ii) from patient plasma and with [$^2$H$_0$]-GP (i) from control plasma. Both chromatograms are plotted on an identical intensity scale. The lower panels are mass spectra recorded at peak apex of 7.47 min and 7.16 min, respectively. The chromatograms define the inborn error of metabolism to be oxysterol 7α-hydroxylase deficiency.

FIGS. 4A and 4B relate to the diagnosis of oxysterol 7α-hydroxylase deficiency. This deficiency may be diagnosed by the use of charge tags as illustrated in FIG. 4. Thus, FIG. 4(A) shows RIC of 539.4363 and 534.4054 corresponding to [M]$^+$ ions of monohydroxycholesterols (HC) labelled with [$^2$H$_5$]-GP (ii) from patient plasma and with [$^2$H$_0$]-GP (i) from control plasma. Both chromatograms are plotted on an identical intensity scale. FIG. 4(B) shows RIC of 553.4155 and 548.3847 corresponding to [M]$^+$ ions of 3β-hydroxycholest-5-enoic acid (HCA) labelled with [$^2$H$_5$]-GP (ii) from patient plasma and with [$^2$H$_0$]-GP (i) from control plasma. Both chromatograms are plotted on an identical intensity scale. The lower panels in (A) and (B) are mass spectra recorded at peak apex of 7.47 min and 7.16 min, respectively. The chromatograms presented in (A) and (B) define the inborn error of metabolism to be oxysterol 7α-hydroxylase deficiency.

Figure 4C:
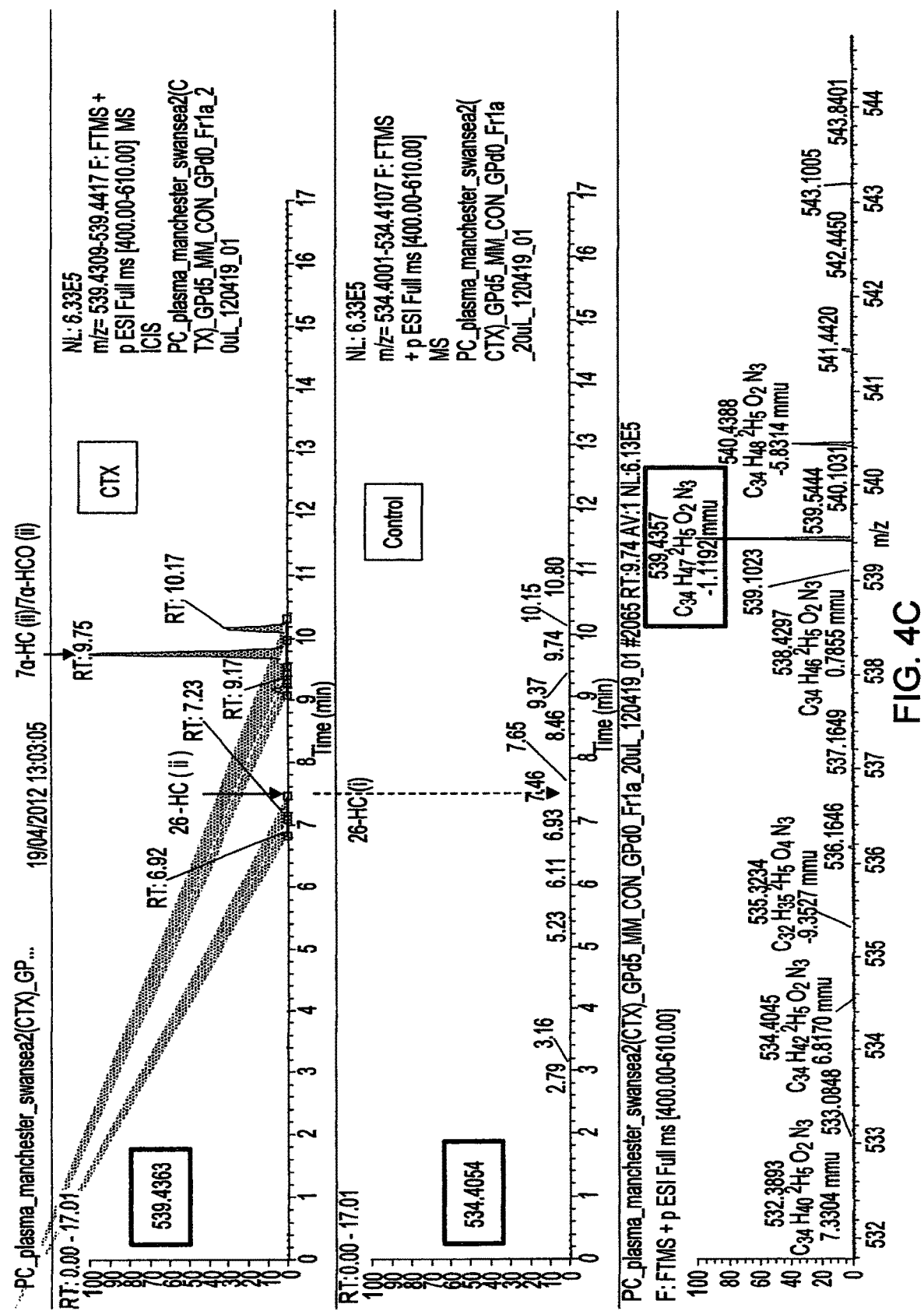
FIG. 4C depicts characterisation of inborn errors of metabolism from patient plasma, with RIC of m/z 539.4363 and 534.4054 corresponding to [M]$^+$ ions of monohydroxycholesterols and hydroxycholest-4-en-3-ones (HCO) labelled with [$^2$H$_5$]-GP (ii) from a different patient plasma and with [$^2$H$_0$]-GP (i) from control plasma. Both chromatograms are plotted on an identical intensity scale. The lower panel shows the mass spectrum at the peak apex of 9.75 min. The chromatograms define the inborn error of metabolism to be CTX.
Figure 4D:
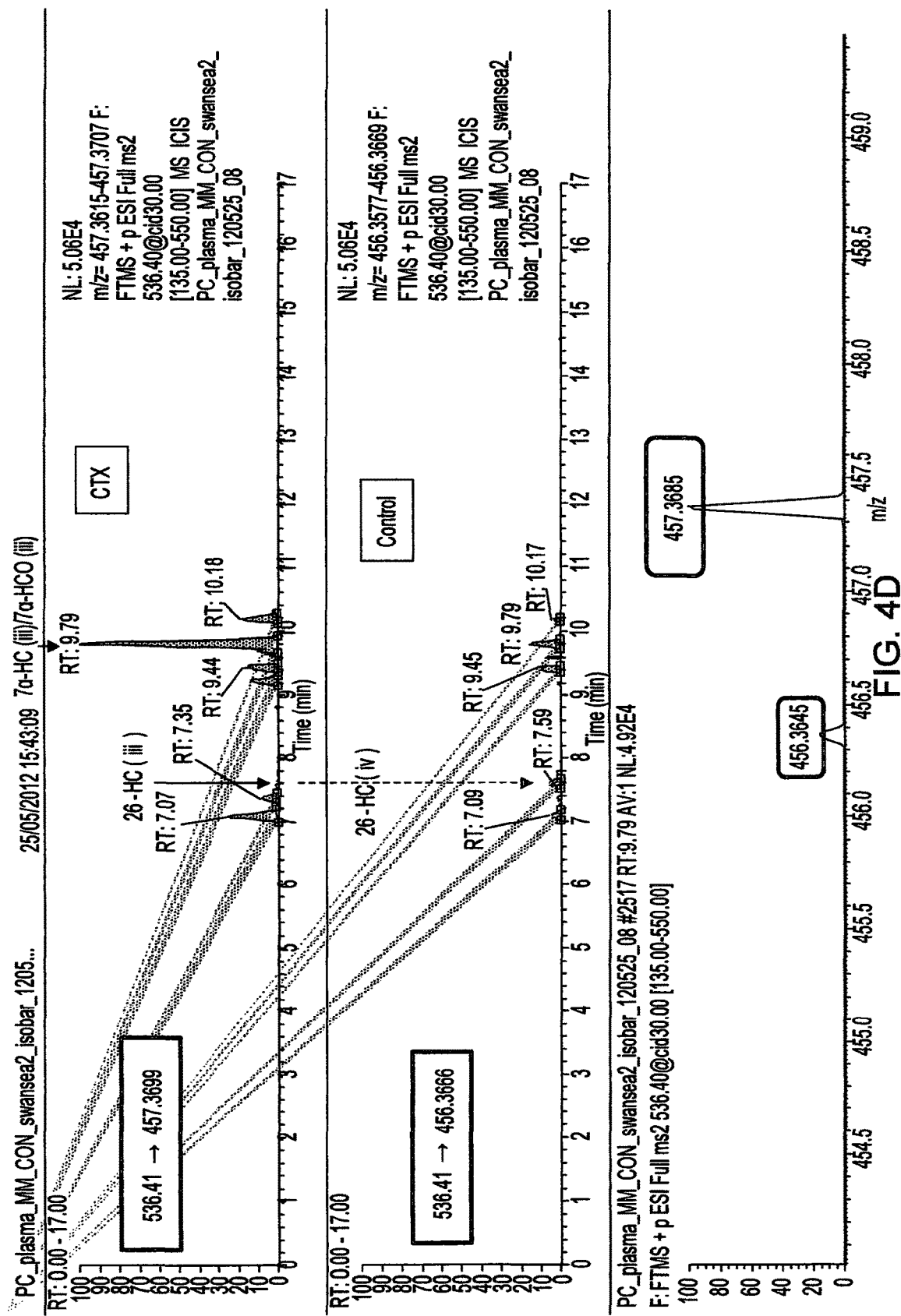
FIG. 4D depicts characterisation of inborn errors of metabolism from patient plasma, with MS$^2$ RIC of m/z 457.3699 and 456.3666 corresponding to [M-Py]$^+$ ions of monohydroxycholesterols and hydroxycholestenones labelled with [$^{13}$C$_2$]-GP (iii) from patient plasma and with [$^{13}$C$^{15}$N]-GP (iv) from control plasma. Both chromatograms are plotted on an identical intensity scale. The lower panel shows the MS$^2$ spectrum acquired at the peak apex of 9.79 min. The chromatograms define the inborn error of metabolism to be CTX.
Figure 4E:
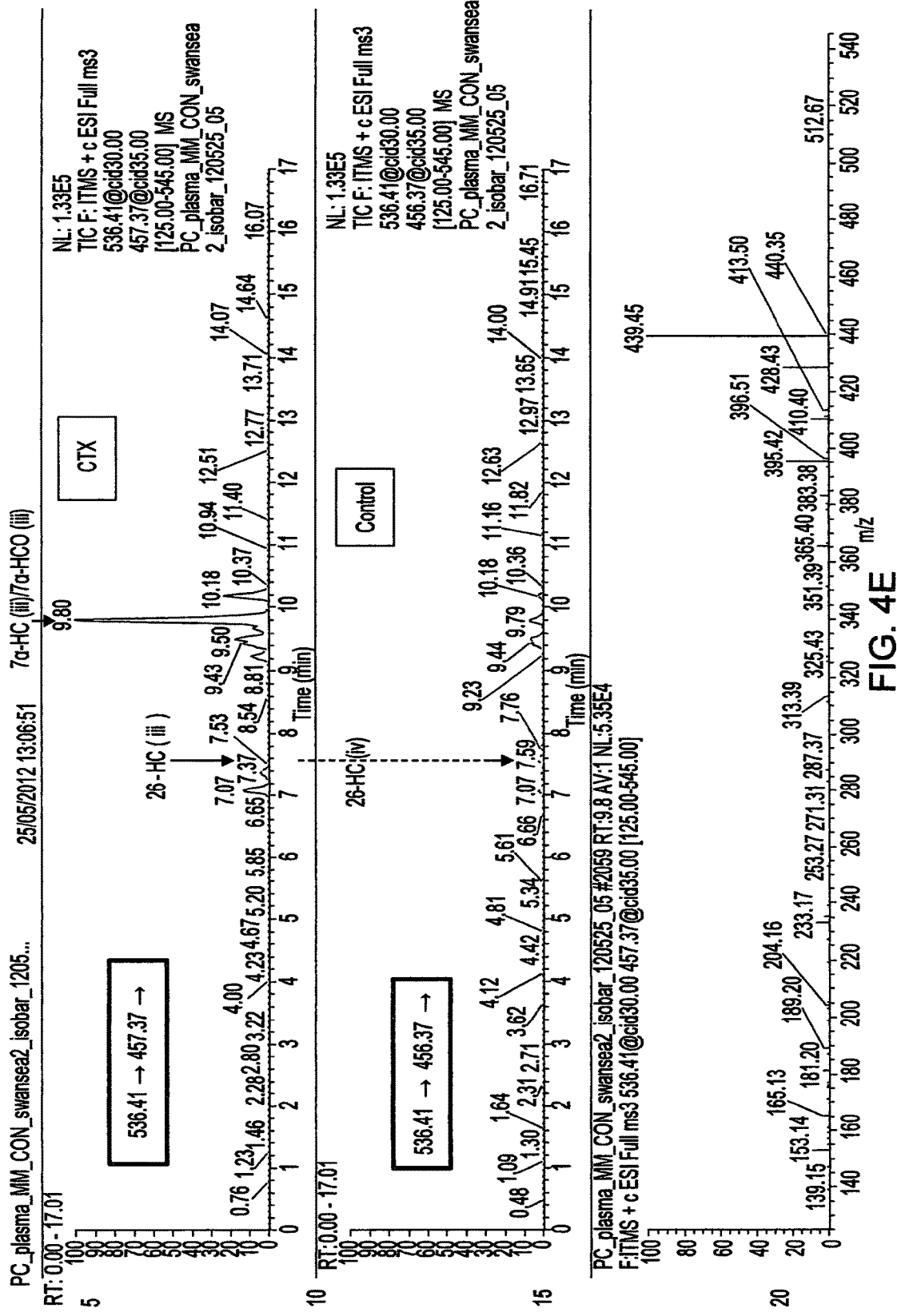
FIG. 4E depicts characterisation of inborn errors of metabolism from patient plasma, with MS$^3$ total ion chromatogram (TIC) of monohydroxycholesterols and hydroxycholest-4-en-3-ones labelled with [$^{13}$C$_2$]-GP (iii) from patient plasma and with [$^{13}$C$^{15}$N]-GP (iv) from control plasma. Both chromatograms are plotted on an identical intensity scale. The lower panel shows the MS$^3$ spectrum recorded at the peak apex 9.80 min. The chromatograms define the inborn error of metabolism to be CTX.
Figure 4F:
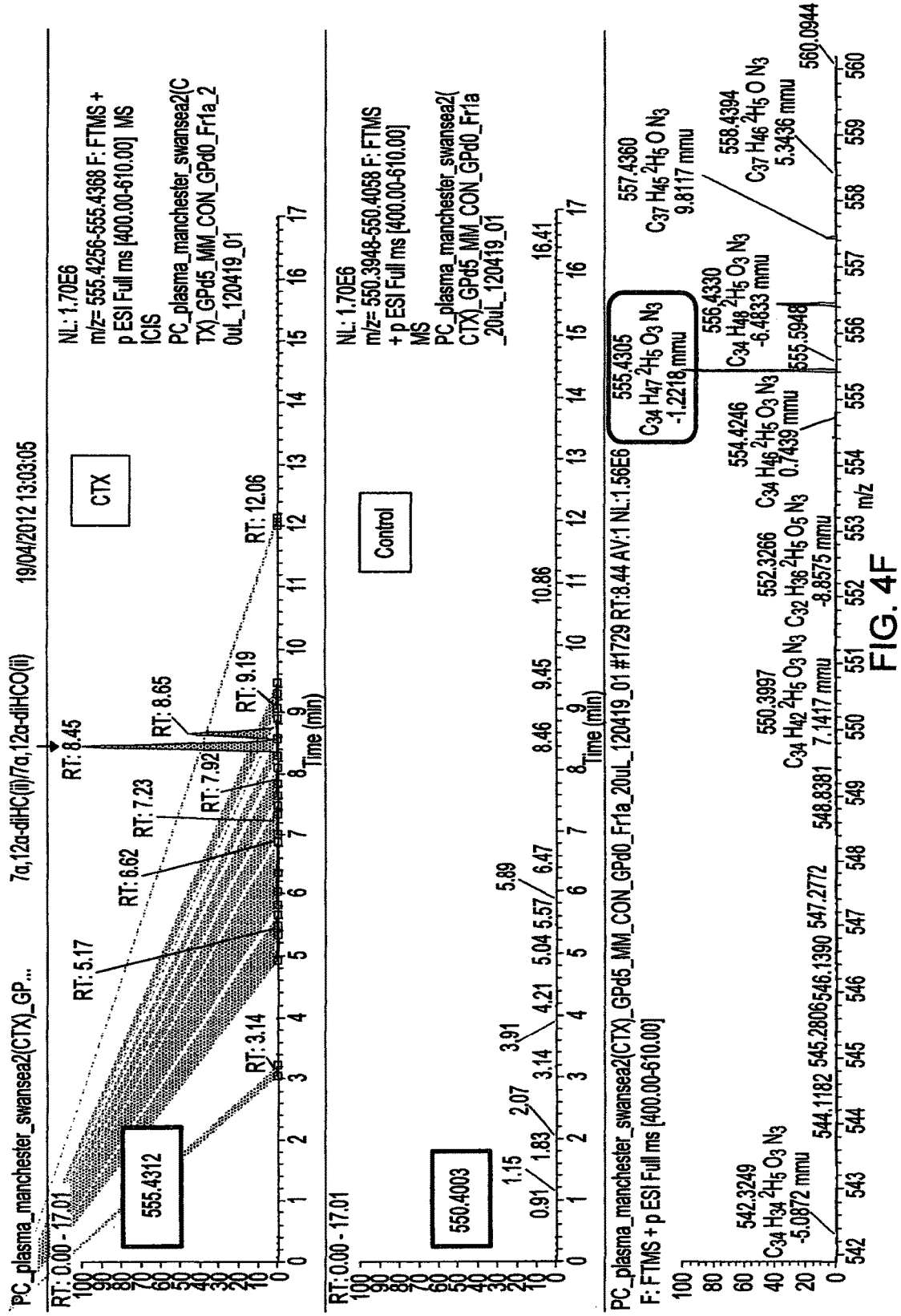
FIG. 4F depicts characterisation of inborn errors of metabolism from patient plasma, with RIC of m/z 555.4312 and 550.4003 corresponding to [M]$^+$ ions of dihydroxycholesterol (diHC) and dihydroxyoxocholesterol (diHCO) labelled with [$^2$H$_5$]-GP (ii) from patient plasma and with [$^2$H$_0$]-GP (i) from control plasma. Both chromatograms are plotted on an identical intensity scale. The lower panel shows the mass spectrum recorded at the peak apex of 8.45 min. The chromatograms define the inborn error of metabolism to be CTX.

CTX, like oxysterol 7α-hydroxylase deficiency, can present in early infancy as cholestatic liver disease and in adult life as spastic paraparesis (Clayton, 2011). CTX is a consequence of mutations in the CYP27A1 gene. It is easily diagnosed using quantitative charge-tags by the absence of peaks corresponding to (25R)26-hydroxycholesterol and 3β-hydroxycholest-5-enoic acid in the appropriate RIC (FIG. 4C-4E). Diagnosis can be confirmed by high levels of 7α-hydroxycholest-4-en-3-one and of 7α,12α-dihydroxycholest-4-en-3-one (FIG. 4C-4F).

Figure 5A:
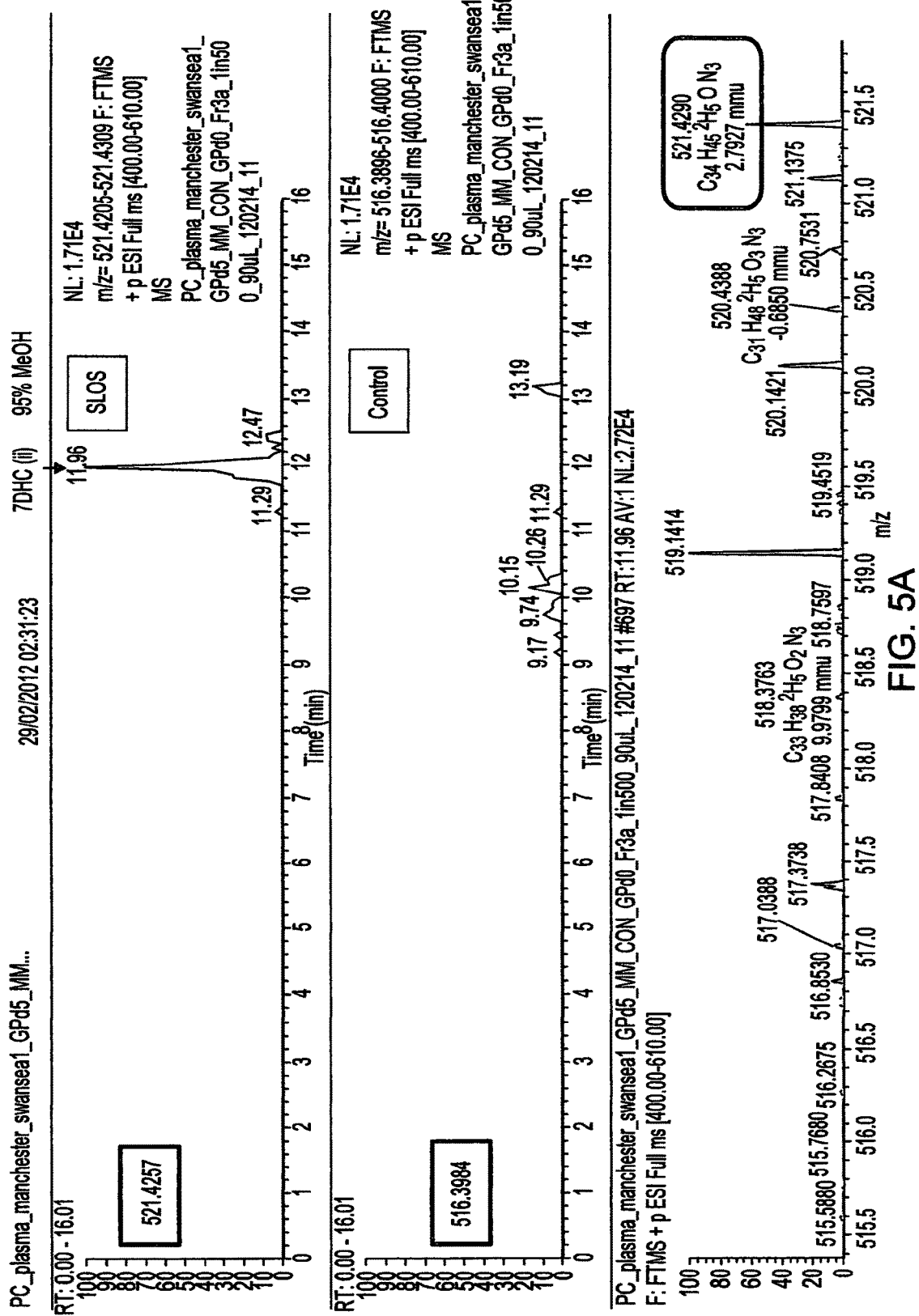
FIG. 5A shows RIC of 521.4257 and 516.3948 corresponding to [M]$^+$ ions of dehydrocholesterols (dHC) labelled with [$^2$H$_5$]-GP (ii) from patient plasma and with [$^2$H$_0$]-GP (i) from control plasma. Both chromatograms are plotted on an identical intensity scale. The lower panel shows the mass spectrum recorded at the peak apex of 11.96 min.
Figure 5B:
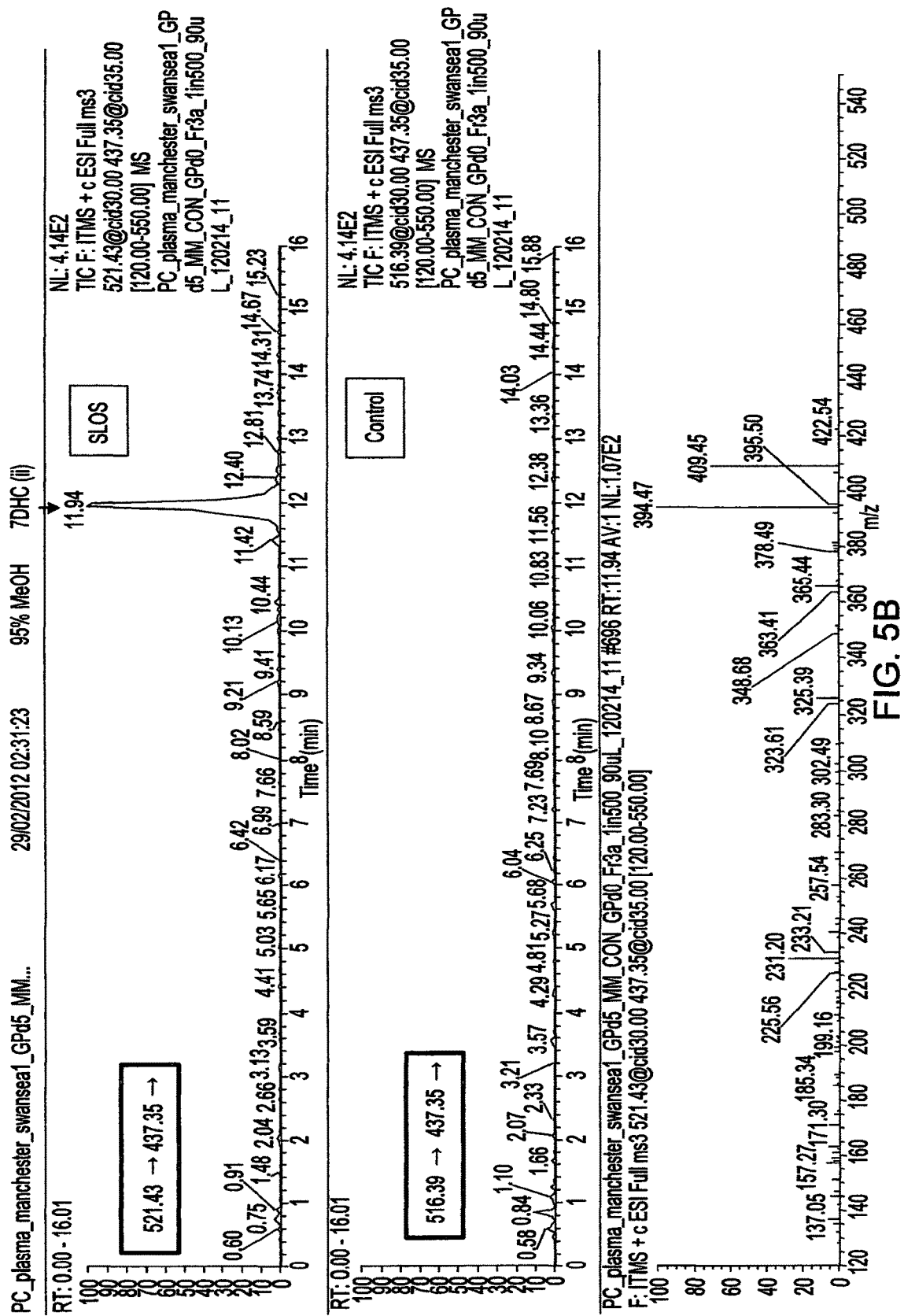
FIG. 5B shows MS$^3$ TIC of dehydrocholesterols labelled with [$^2$H$_5$]-GP (ii) from patient plasma and with [$^2$H$_0$]-GP (i) from control plasma. Both chromatograms are plotted on an identical intensity scale. Data was obtained by on the LTQ-Orbitrap. The lower panel shows the MS$^3$ spectrum recorded at the peak apex of 11.94 min.

SLOS is a genetic defect of cholesterol biosynthesis. The defective enzyme is 7-dehydrocholesterol reductase (Dhcr7) which reduces 7-dehydrocholesterol to cholesterol. In plasma from control populations the level of 7-dehydrocholesterol is usually two-three orders of magnitude lower than that of cholesterol, while in SLOS patients its level is elevated depending on the severity of disease (Griffiths et al., 2008). This is nicely illustrated in the LC-MS RICs for patient and control plasma derivatised with [$^2$H$_5$]-GP (ii) and [$^2$H$_0$]-GP (i), respectively; and in the comparative total ion chromatograms (TICs) for the MS$^3$ transitions [M]$^+$→[M-Py]$^+$→ for plasma samples from a control and SLOS patient similarly derivatised (FIGS. 5A & 5B). For a disease such as SLOS diagnosis can be achieved from blood spots on filter paper in the absence of LC separation where the enhanced level of 7-dehydrocholesterol is evident from the ES-MS. Using this simplest methodology it is even possible to determine the severity of the disease

Example 8—Comparing Control, MCI and AD Patient Plasma

Figure 7A:
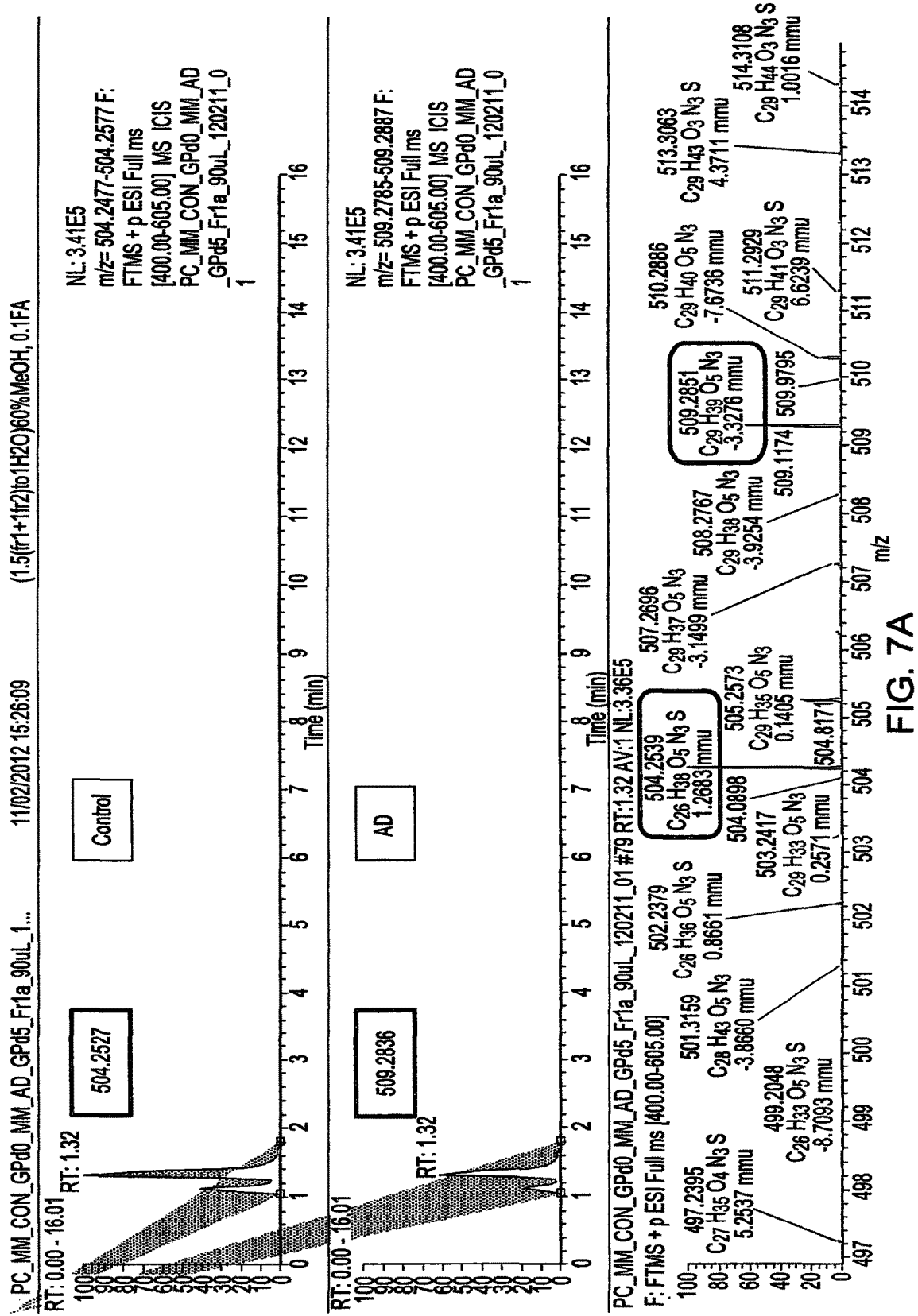
FIG. 7A shows analysis of pooled samples of plasma from controls, patients with Alzheimer's disease (AD) and mild cognitive impairment (MCI) and demonstrates that isomers of androstanolone 3-sulphate show differential abundance in the three samples.
Figure 7B:
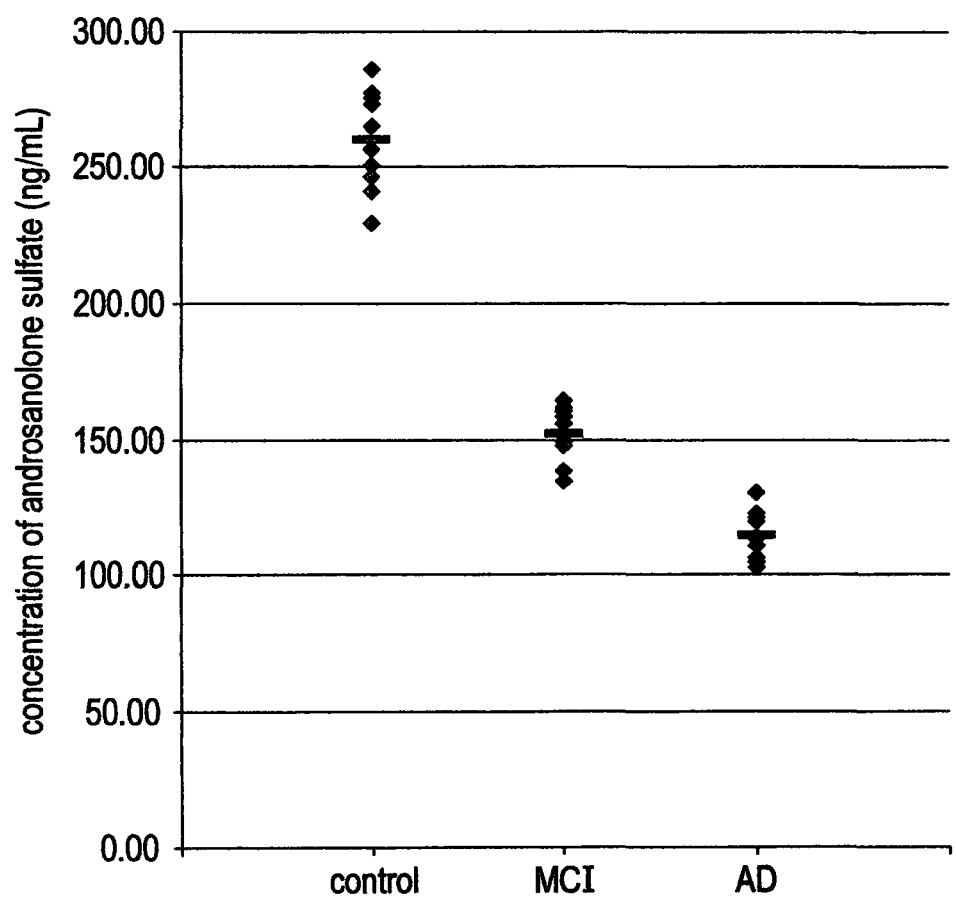
FIG. 7B shows that levels of isomers of androstanolone 3-sulphate fall from control to MCI to AD patients.

About a quarter of the body cholesterol is found in brain (Dietschy and Turley, 2004 J. Lipid Res. 45, 1375-1397), hence it is not surprising that cholesterol, its precursors and metabolites have been suggested as markers of AD disease (Griffiths and Wang, 2009, Eur. J. Lipid Sci. Technol. 111, 14-38). As a prelude to analyzing a large batch of plasma samples from controls, AD and MCI patients and determining their individual steroid profiles we have analysed three pooled samples representing these three groups. Steroids found to show differential abundance in the three samples are isomers of androstanolone 3-sulphate (FIG. 7A). Interestingly, their level falls from control to MCI to AD patients (FIG. 7B). This suggests that levels of isomers of androstanolone 3-sulphate may represent potential markers for the progression to MCI and subsequently AD. Current studies are now being performed to confirm this finding with individual plasma samples.

The invention claimed is:

1. A method for the quantitative detection of oxosteroids and hydroxy steroids in a sample, the method comprising:
   i. reacting a first portion of the sample with a first member of a pair of quantitative charge tags of formula (I) or formula (II);
   wherein R is hydrogen, $C_{1-4}$ alkyl or aryl, $OR^1$ or $NR^1R^2$,
   each $R^1$ and $R^2$ is $C_{1-3}$ alkyl or $R^1$ and $R^2$ together with the nitrogen atom to which they are attached form a 5- or 6-membered heteroalkyl ring;
   each $R^3$ is independently $C_{1-3}$ alkyl; and
   X is a halide ion;
   ii. reacting a second portion of the sample with an agent capable of oxidising an OH group to a carbonyl group;
   iii. reacting the product of step (ii) with a second member of a pair of quantitative charge tags of formula (I) or formula (II);
   iv. combining the products of steps (i) and (iii);
   v. conducting mass spectrometry on the combined product of step (iv) and determining the quantities therein of compounds labelled with the first and second members of the pair of quantitative charge tags, thereby providing quantitative detection of both oxosteroids and hydroxy steroids in a single analysis.

2. The method as claimed in claim 1, wherein the first and second portions of the sample are of equal volume.

3. The method as claimed in claim 1 wherein the quantitative charge tags are differential mass tags and the mass spectrometry of step (v) is liquid chromatography-mass spectrometry (LC-MS) or HPLC-MS.

4. The method as claimed in claim 1 wherein the quantitative charge tags are isobaric mass tags and the mass spectrometry of step (v) is an MS/MS method.

5. The method as claimed in claim 1 wherein the sample is prepared from a body fluid, for example whole blood, plasma, serum, cerebrospinal fluid, sputum, tears, sweat or urine; or from a specimen of tissue, hair, nails by extraction of the steroids into a solvent.

6. A method for the quantitative detection of oxosteroids and hydroxy steroids in a sample, the method comprising:
   i. reacting the sample with a first member of a pair of quantitative charge tags of formula (I) or formula (II) wherein R is hydrogen, $C_{1-4}$ alkyl or aryl, $OR^1$ or $NR^1OR^2$;
   each $R^1$ and $R^2$ is $C_{1-3}$ alkyl or $R^1$ and $R^2$ together with the nitrogen atom to which they are attached form a 5- or 6-membered heteroalkyl ring;
   each $R^3$ is independently $C_{1-3}$ alkyl;
   and X is a halide ion;
   ii. reacting a reference composition with a second member of a pair of quantitative charge tags of formula (I) or formula (II);
   iii. combining the products of steps (i) and (ii);
   iv. conducting mass spectrometry on the combined product of step (iii) and determining the quantities therein of compounds labelled with the first and second members of the pair of quantitative charge tags, thereby providing quantitative detection of both oxosteroids and hydroxy steroids in a single analysis.

7. The method according to claim 6 wherein both the sample and the reference composition are reacted with an agent capable of oxidising an OH group to a carbonyl group before reaction with the quantitative charge tags.

8. The method as claimed in claim 6, wherein the sample and the reference composition are of equal volume.

9. The method as claimed in claim 6 wherein the quantitative charge tags are differential mass tags and the mass spectrometry of step (vi) is liquid chromatography-mass spectrometry (LC-MS) or HPLC-MS.

10. The method as claimed in claim 6 wherein the quantitative charge tags are isobaric mass tags and the mass spectrometry of step (vi) is an MS/MS method.

11. The method as claimed in claim 6 wherein the method is repeated for a further sample using the same or a different reference composition.

12. A method for the quantitative determination of oxosteroids and hydroxy steroids in a sample comprising:
   i. reacting a first portion of the sample with a first member of a first pair of quantitative charge tags of formula (I) or formula (II);
   wherein R is hydrogen, $C_{1-4}$ alkyl or aryl, $OR^1$ or $NR^1R^2$;
   each $R^1$ and $R^2$ is $C_{1-3}$ alkyl or $R^1$ and $R^2$ together with the nitrogen atom to which they are attached form a 5- or 6-membered heteroalkyl ring;
   each $R^3$ is independently $C_{1-3}$ alkyl; and
   X is a halide ion;
   ia. reacting a first portion of a reference composition with a first member of a second pair of quantitative charge tags of formula (I) or formula (II);
   ii. reacting a second portion of the sample with an agent capable of oxidising an OH group to a carbonyl group;
   iia. reacting a second portion of a reference composition with an agent capable of oxidising an OH group to a carbonyl group;
   iii. reacting the product of step (ii) with a second member of a first pair of quantitative charge tags of formula (I) or formula (II);
   iiia. reacting the product of step (iia) with a second member of a second pair of quantitative charge tags of formula (I) or formula (II);
   iv. combining the products of steps (i) and (iii);
   v. conducting mass spectrometry on the combined product of step (iv) and determining the quantities therein of compounds labelled with the first and second members of the pair of quantitative charge tags, thereby providing quantitative detection of both oxosteroids and hydroxy steroids.

13. The method as claimed in claim 12 wherein the portions of sample and reference composition are of equal volume.

14. The method as claimed in claim 12 wherein the first pair of quantitative charge tags are differential mass tags and the second pair of quantitative charge tags are isobaric mass tags.

15. The method as claimed in claim 12 wherein the first pair of quantitative charge tags are isobaric mass tags and the second pair of quantitative charge tags are differential mass tags.

16. The method as claimed in claim 12 further comprising repeating steps (i) to (iii) with a further sample and a further pair of quantitative mass tags and combining the labelled further sample portions with the product of step (iv) before carrying out mass spectrometry.

* * * * *